US012390115B2

(12) United States Patent
Groppo

(10) Patent No.: US 12,390,115 B2
(45) Date of Patent: Aug. 19, 2025

(54) PHOTOPLETHYSMOGRAPHY BASED DETECTION OF TRANSITIONS BETWEEN AWAKE, DROWSINESS, AND SLEEP PHASES OF A SUBJECT

(71) Applicant: SLEEP ADVICE TECHNOLOGIES S.R.L., Turin (IT)

(72) Inventor: Sara Groppo, Turin (IT)

(73) Assignee: SLEEP ADVICE TECHNOLOGIES S.R.L., Turin (IT)

( * ) Notice: Subject to any disclaimer, the term of this patent is extended or adjusted under 35 U.S.C. 154(b) by 1151 days.

(21) Appl. No.: 17/271,499

(22) PCT Filed: Aug. 29, 2019

(86) PCT No.: PCT/EP2019/073148
§ 371 (c)(1),
(2) Date: Feb. 25, 2021

(87) PCT Pub. No.: WO2020/043855
PCT Pub. Date: Mar. 5, 2020

(65) Prior Publication Data
US 2022/0015654 A1    Jan. 20, 2022

(30) Foreign Application Priority Data

Aug. 29, 2018 (EP) .................................. 18191543
Aug. 29, 2018 (EP) .................................. 18191547
Mar. 4, 2019 (EP) .................................. 19160639

(51) Int. Cl.
*A61B 5/024* (2006.01)
*A61B 5/00* (2006.01)
*A61B 5/18* (2006.01)

(52) U.S. Cl.
CPC ...... *A61B 5/02416* (2013.01); *A61B 5/02405* (2013.01); *A61B 5/18* (2013.01);
(Continued)

(58) Field of Classification Search
CPC ............ A61B 5/02405; A61B 5/02416; A61B 5/4812; A61B 5/7257
See application file for complete search history.

(56) References Cited

U.S. PATENT DOCUMENTS

2007/0078351 A1    4/2007   Fujita et al.
2011/0124979 A1    5/2011   Heneghan et al.
(Continued)

FOREIGN PATENT DOCUMENTS

KR        101601895 B1       3/2016

OTHER PUBLICATIONS

Korean First Office Action in KR Application No. 201980057110.2, mailed Sep. 27, 2023, an English Translation is attached hereto. (15 pages).

*Primary Examiner* — Tse W Chen
*Assistant Examiner* — Michael A Catina
(74) *Attorney, Agent, or Firm* — Leason Ellis LLP

(57) ABSTRACT

A smart system comprising a contact or contactless PPG sensor to output a PPG signal; and an electronic processing system in communication with the PPG sensor to acquire the PPG signal therefrom and analyse the PPG signal in one or both of time and frequency domains to real-time predict transitions between awake and sleep phases of a subject based on an output of the analysis, either wearing the smart wearable system equipped with the contact PPG sensor or remotely monitored by the contactless PPG sensor.

16 Claims, 18 Drawing Sheets

(52) U.S. Cl.
CPC .......... *A61B 5/4812* (2013.01); *A61B 5/7257* (2013.01); *A61B 5/7267* (2013.01)

(56) References Cited

U.S. PATENT DOCUMENTS

| | | |
|---|---|---|
| 2014/0088378 A1 | 3/2014 | Muzet |
| 2018/0064388 A1* | 3/2018 | Heneghan .............. A61B 5/743 |
| 2018/0214089 A1 | 8/2018 | Kannan et al. |
| 2019/0223773 A1* | 7/2019 | Galm ..................... A61B 5/165 |

* cited by examiner

[PPG Fundamental Frequency - Hz]

PHOTOPLETHYSMOGRAPHY BASED DETECTION OF TRANSITIONS BETWEEN AWAKE, DROWSINESS, AND SLEEP PHASES OF A SUBJECT

CROSS-REFERENCE TO RELATED PATENT APPLICATIONS

This patent application is a U.S. National Phase Application under 35 U.S.C. § 371 of International Patent Application No. PCT/EP2019/073148, filed Aug. 29, 2019, which claims the priority of European patent applications Nos. 18191543.0 and 18191547.1 filed on Aug. 29, 2018, and of European patent application No. 19160639.1 filed on Mar. 4, 2019, all of which are incorporated by reference, as if expressly set forth in their respective entities herein.

TECHNICAL FIELD OF THE INVENTION

The present invention relates to automatic and adaptive detection of aWake (W), Drowsiness (D), and Sleep (S) phases of a subject, and prediction of transitions between W, D, and S phases.

STATE OF THE ART

As is known, non-invasive recognition of different behavioural phases (W, D, S) of individuals is a problem that concerns some of the main areas of modern life, such as public health and safety in transportation and working environments, with important consequences in socio-economic terms and with important impulses to research and development area.

With regard to public health, normally an adult subject on average spends about ⅓ of his day sleeping and Sleep Medicine has only recently been recognized as a specialty of medicine. Its development is based on an increasing amount of knowledge concerning the physiology of sleep, circadian biology, and the pathophysiology of sleep disorders. Despite the young life of this branch of medicine, the International Classification of Sleep Disorders (ICSD) has identified over 80 different sleep disorders. The effects of sleep disorders are extensive, impacting sufferers physically, psychologically and financially. Excessive daytime sleepiness (EDS) have been shown to be the second largest group of sleep disorders. Up to 40% of the industrial countries adult population experience problems with falling asleep or daytime drowsiness which are assumed to be due not only to disturbed sleep patterns classified as a sleep pathology, but also by very common and possibly environment linked conditions such as a state of deprivation of sleep, physical or mental stress, alcohol consume, sleeping pills assumption and any context where individuals perform repetitive actions. All these conditions can also overlap in certain situations by mutually reinforcing.

Therefore, drowsiness is synonymous with sleepiness, which simply means an inclination to fall asleep derived by widespread conditions that can affect anyone, even healthy and young people, contributing to personal injury, disability and poor work performance due to a progressive reduction in the level of attention and degree of consciousness of the subject. It is a transition process between two physiological states: awake and sleep.

Currently, the gold standard of the tests performed by sleep medicine for the study of human sleep disorders and for the identification of the main human behavioural states, in particular the W, D, and S phases, is the PolySomnoGraphy (PSG). This is an extremely complex instrumental examination that involves the application on the patient of numerous sensors (from a minimum of 10 to over 30) in direct contact with various parts of the body, both external and internal, for example skin, scalp, nasal cavities, oesophageal lumen. Through this set of sensors, the polysomnograph is able to record for hours, usually for one night, the main physiological functions of the patient, such as brain electrical activity (EEG), cardiorespiratory activity, body movements, eyes movements, muscle tone, endoesophageal pressure, etc.

FIGS. 1A and 1B show the assembly of the PSG on a patient and the display of the recorded signals on a personal computer, respectively.

The PSG is a useful but demanding exam for the patient and requires highly specialized technical staff for the assembly of the instrumentation on the subject to be studied and doctors with specific skills in sleep medicine for the analysis and interpretation of the recorded data. Moreover, PSG is very expensive and is limited by the number of beds available in the study centre and the number of specialists available to read and assess the data.

With regard to transportation and working environments, drowsiness seriously impairs peoples' ability either to drive or to accomplish their activity, as they find it difficult to maintain their attention on the task. This is a harmful risk on the road and, more generally, on industrial activities (e.g. working in a production plant, controlling a robot, operating a welding machine, etc.). It is reported that 35%-45% of road accidents are caused by drowsy driving (i.e., driving while sleepy or fatigued). In the year 2009, the US National Sleep Foundation (NSF) reported that 54% of adult drivers have driven a vehicle while feeling drowsy and 28% of them actually fell asleep.

According to the information from NHTSA (National Highway Traffic Safety Administration) of the United States (US), there are about 100,000 crashes caused by driver drowsiness or fatigue annually, and these accidents cause more than 1500 fatalities and 71,000 injuries. In Europe, driver fatigue causes about 6000 deaths every year and many studies claim that the main cause of the 15%-20% of all traffic accidents is driver fatigue.

Mental fatigue and sleepiness accidents do not only exist in ordinary road traffic, but also in air and rail transport sector and in industrial sector where subjects use or control hazardous machineries. Compared with the normal civil field, accidents in these industries would cause much worse outcomes, even a disaster like for example the Chernobyl one.

Consequently, an increasing amount of R&D and more studies are focused on the design of automatic systems and methodologies to deal with the above-mentioned social problems.

As regards identification of driving drowsiness, current related researches have used the following measures:

Vehicle-based measures: deviations from lane position, movement of the steering wheel, pressure on the acceleration pedal, etc. are constantly monitored and any change in these that crosses a specified threshold indicates a significantly increased probability that the driver is drowsy;

Driver behaviour measures including yawning, eyes closure, eyes blinking, head pose, etc., is monitored through a camera and the driver is alerted if any of these drowsiness symptoms are detected; and Physiological measures. Many studies and researches have been conducted to determine the relationship between driver's drowsiness and some physiological data studied through the analysis of the respective signals: electrocardiogram (ECG) for heart rate variability, electroencephalogram (EEG) for electrical cerebral activity, electromyogram (EMG) for muscular activity, electrooculogram (EoG) for ocular movements.

Reliability and accuracy in driver drowsiness detection by using all these measures is to be considered insufficient because of some fundamental limitations:

Vehicle-based and driver behavioural measures work in very limited conditions because they are too dependent on external factors like geometric characteristics of the road, road marking, climatic and lighting conditions. Moreover, they are susceptible to visual barriers such as driver face position and glasses wearing. Additionally, the colour of the skin and the presence of the beard could influence the reconstruction of the facial contours and characteristics, including the position/movement of the eyes and the mouth; and Physiological measures currently studied present the issue of the intrusive nature of most of the sensors they used. Moreover, many studies have determined that all these measures are poor predictors because they become clearly effective only after the driver starts sleeping, which is too late for a preventive action.

US 2018/214089 A1 discloses drowsiness onset detection implementations that predict when a person transitions from a state of wakefulness to a state of drowsiness based on heart rate information. Appropriate action is then taken to stimulate the person to a state of wakefulness or notify other people of their state (with respect to drowsiness/alertness). This generally involves capturing a person's heart rate information over time using one or more heart rate (HR) sensors and then computing a heart-rate variability (HRV) signal from the captured heart rate information. The HRV signal is analysed to extract features that are indicative of an individual's transition from a wakeful state to a drowsy state. The extracted features are input into an artificial neural net (ANN) that has been trained using the same features to identify when an individual makes the aforementioned transition to drowsiness. Whenever an onset of drowsiness is detected, a warning is initiated.

US 2014/088378 A1 discloses a system and a method for determining sleep, sleep stage and/or sleep stage transition of a person, including heart rate detecting means configured for detecting a heart rate of the person, movement detecting means configured for detecting a movement of a part of the body of the person, where the detected movement is caused by a skeletal muscle of the body, recording means configured for recording the detected heart rate and the detected movement of the part of the body, heart rate classifying means configured for classifying the recorded heart rate of the person into at least one heart rate class at least one heart rate variability class, movement classifying means configured for classifying the recorded movement into at least one movement class, and determining means configured for determining sleep, a sleep stage, a sleep stage transition and/or a sleep event of the person based at least partially on the at least one heart rate class and the at least one movement class.

US 2018/064388 A1 discloses a system, a computer-readable storage medium, and a method capable of, directly or indirectly, estimating sleep states of a user based on sensor data from movement sensors and/or optical sensors. A typical photoplethysmographic (PPG) signal, such as may be output by an optical heart rate sensor such as those discussed herein, may provide a periodic signal that indicates heart rate. The PPG signal is typically the voltage measured by an optical heart rate sensor and reflects the volume changes of blood passing through blood vessels in the tissue under the sensor. As the heart beats, the volume of blood in the blood vessels changes with each beat. Thus, the peak/trough pattern seen in the raw PPG signal reflects the underlying heartbeats of the person. By detecting the peaks (or, alternatively, the troughs) of the PPG signal, the person's cardiac activity can be determined. Such a signal is typically analysed to determine how many peaks in the signal occur within a given interval, and this is indicative of the beats per minute. A peak-counting algorithm may be used to determine the locations of the peaks, e.g., the data may be analysed to find maximum or minimum values within specified windows of time. For example, a window of time may be defined between every time the PPG signal exceeds a certain level and then subsequently falls below another level—the maximum value within that window of time may be identified as a "peak." The identified peaks may also be checked to ensure that they are "physiologically reasonable," i.e., they are not too far apart or close together that they would be physiologically impossible.

US 2007/078351 A1 discloses a fatigue degree measurement device, a fatigue detection device and a computer program to be used therein. The fatigue degree measurement device includes a living body signal peak value detecting means to detect the peak values of respective cycles of the original waveform of the living body signal data; a power value calculating means to calculate the difference between a peak value on the upper limit side and a peak value on the lower limit side for every prescribed time period from respective peak values obtained by the living body signal peak value detecting means to set the difference as a power value; and a power value inclination calculating means 25 to determine the inclination of the power value, to calculate an integral value by absolute value treatment of the time series signals of the inclination of the power values to determine the integral value as the degree of fatigue. As a result, it becomes possible to realize quantification of a human fatigue degree.

OBJECT AND SUMMARY OF THE INVENTION

The object of the present invention is to provide a simple, automatic, adaptive, real-time, and cost-effective electronic processing system capable of automatically detecting, through both contact and contactless technologies, and predicting the transitions between the awake (W), drowsiness (D), and sleeping (S) phases of a subject.

According to the present invention, an electronic processing system, a modular composable electronic system, and a software therefor are provided, as claimed in the appended claims.

In a nutshell, the present invention covers two main items: a) an innovative methodology to automatically detect and predict the transitions between the W, D, and S phases of a subject.

The methodology relies on the deep analysis of physiological features primarily extracted through the PhotoPlethysmoGraphy (PPG) technology and includes the additional contribution of the real time assessment of the emotional phases. This method counts on relevant background in the sleep medicine discipline and in particular the "somnificity" concept, which strongly inspired such a multi-factors analysis.

The methodology adopts a very flexible and innovative approach combining time domain analysis with frequency domain analysis. Consequently, it is able to extract a robust set of parameters despite of the, generally, low quality of measured physiological signals.

The methodology includes a learning and adaptive control for the individual self-calibration of physiological parameters of the subject. The process is fully automated, transparent to the user and evolves over the time, thus continuously adjusting the parameters in order to provide the most accurate prediction capability.

The prediction method takes also into account extra context features of the subject, e.g., body movement and temperature, so resulting in a very robust and automated analysis.

b) a modular and composable smart system, hereinafter referred to as Cyber Physical System (CPS), which relies on a very reduced set of physiological parameters, e.g., blood pressure, change in the volume of blood vessels, etc., through the PPG technology, able to non-invasively determine W, D, and S phases of a subject.

The modular composable CPS could support both a contact technology, e.g., wearable, and a contactless technology. The main advantage of such an inherently simple approach primarily based on PPG technology and validated through exhaustive and accurate clinical analysis, is the possibility to implement proprietary algorithms, running in real time on a family of smart systems, for the precise detection and prediction of the drowsiness. Consequently, a wide range of applications, where the drowsiness of the subjects is a relevant factor, can be successfully addressed.

The proposed innovative methodology based on multi-factors extracted through PPG technology is summarised in FIG. 2: from multiple features extracted from multiple sensors towards multiple factors extracted through PPG technology.

DETAILED DESCRIPTION OF PREFERRED EMBODIMENTS OF THE INVENTION

The present invention will now be described in detail with reference to the accompanying drawings in order to allow a skilled person to implement it and use it. Various modifications to the described embodiments will be readily apparent to those of skill in the art and the general principles described may be applied to other embodiments and applications without however departing from the protective scope of the present invention as defined in the appended claims. Therefore, the present invention should not be regarded as limited to the embodiments described and illustrated herein, but should be allowed the broadest protection scope consistent with the features described and claimed herein.

Unless otherwise defined, all technical and scientific terms used herein have the same meaning commonly understood by one of ordinary skill in the art to which the invention belongs. In case of conflict, the present specification, including the definitions provided, will control. Furthermore, the examples are provided for illustrative purposes only and as such should not be considered limiting.

In particular, the block diagrams included in the attached figures and described below are not to be understood as a representation of the structural features, i.e. constructional limitations, but must be understood as a representation of functional features, i.e. intrinsic properties of the devices defined by the effects obtained, that is to say functional restrictions, which can be implemented in different ways, so as to protect the functionalities thereof (operational capability).

In order to facilitate the understanding of the embodiments described herein, reference will be made to some specific embodiments and a specific language will be used to describe the same. The terminology used herein is used for the purpose of describing particular embodiments only, and is not intended to limit the scope of the present invention.

PhotoPlethysmoGraphy (PPG) technology is a non-invasive optical technique for detecting microvascular blood volume changes in tissue bed beneath the skin, which are due to the pulsatile nature of the circulatory system.

PPG has important implications for a wide range of applications in cardiovascular system assessment, vital sign monitoring, blood oxygen detection, and became a mandated international standard for monitoring during anaesthesia.

Figure 3:
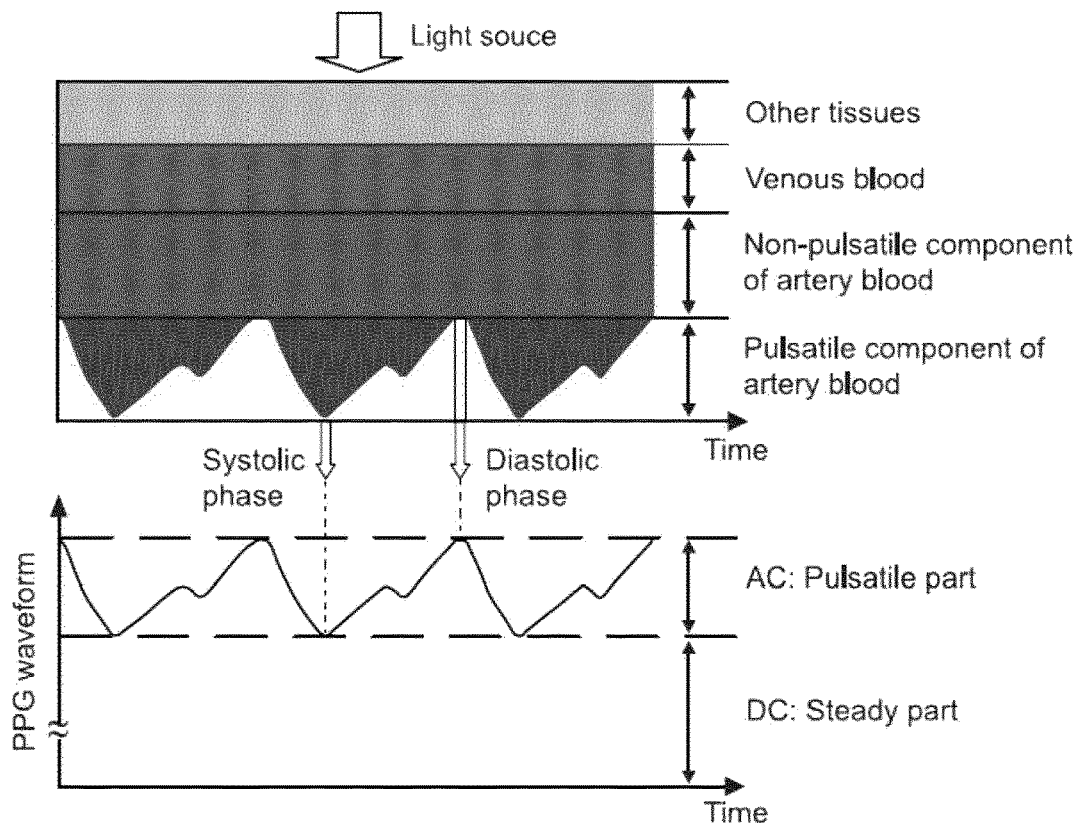
FIG. 3 shows the variation in light attenuation by tissue.

The measured PPG waveform, therefore, comprises a pulsatile (often called "AC") physiological waveform that reflects cardiac synchronous changes in the blood volume with each heartbeat, which is superimposed on a much larger slowly varying quasi-static ("DC") baseline. FIG. 3 shows the variation in light attenuation by tissue.

The DC component contains valuable information about respiration, venous flow, sympathetic nervous system activities, and thermoregulation.

Figure 4:
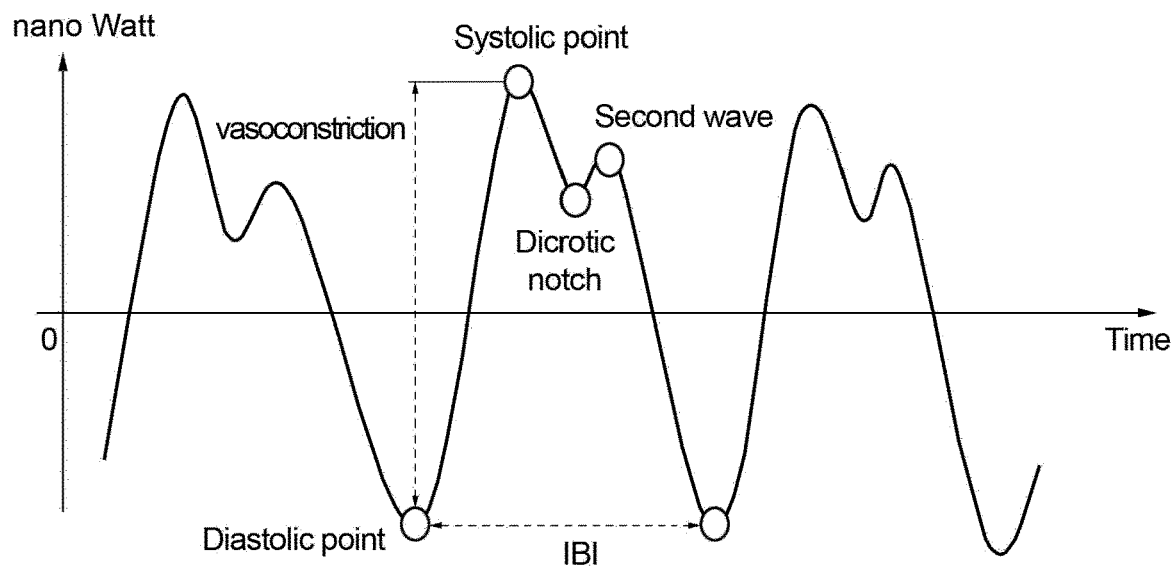
FIG. 4 shows a PPG waveform.

As shown in FIG. 4, the PPG waveform indicates four relevant points that are diastolic points, systolic points, dicrotic notch and dicrotic wave.

Pulse oximetry has become the most used non-invasive measurement of the oxygen saturation (SpO2). Oxygen saturation is defined as the measurement of the amount of oxygen dissolved in blood, based on the detection of Haemoglobin and Deoxyhaemoglobin. The pulse oximeter analyses the light absorption of two wavelengths from the pulsatile-added volume of oxygenated arterial blood (AC/DC) and calculates the absorption ratio.

Active research efforts have shown the great utility of PPG technology well beyond oxygen saturation and heart rate determination. Future trends are being heavily influenced by modern digital signal processing, which is allowing a re-examination of this ubiquitous waveform.

Key to unlock the potential of this waveform is the full access to the raw signal with adequate precision and resolution, combined with new methods of analysis, possibly exploiting the capabilities offered by modern Artificial Intelligence and data science technologies.

Figure 5:
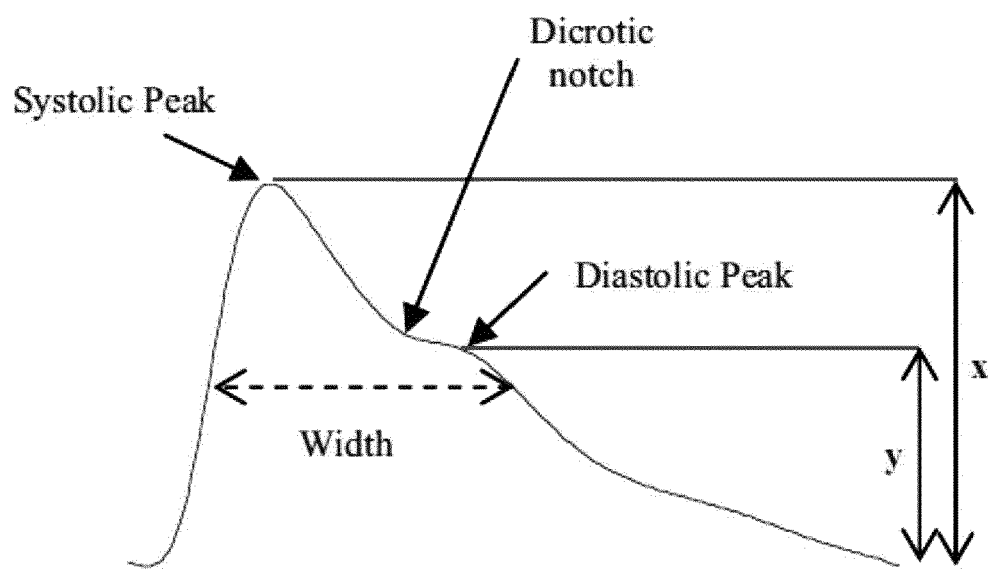
FIG. 5 shows characteristic parameters of a typical PPG waveform, where the amplitude of the systolic peaks is denoted by x and the amplitude of the diastolic peak is denoted by y.

Although the morphology of the PPG signal looks similar to the arterial pressure pulse, the wave contour is not the same. As shown in FIG. 5, looking into the details of PPG waveform a large amount of useful information, about the health status of the subject under analysis can be derived.

Amplitude analysis: one of the more useful PPG features is the waveform amplitude. The amplitude of the PPG signal is directly proportional to the vascular distensibility, over a remarkably wide range of cardiac output. In particular, the systolic amplitude (x) is an indicator of the pulsatile changes in blood volume caused by arterial blood flow around the measurement site. If the vascular compliance is low, for example during episodes of increased sympathetic tone, the pulse oximeter waveform amplitude is also low. With vasodilatation, the pulse oximeter waveform amplitude is increased. It has been suggested that systolic amplitude is potentially a more suitable measure than pulse arrival time for estimating continuous blood pressure.

Rhythm analysis: the PPG waveform can be a useful tool for detecting and diagnosing cardiac arrhythmias, since the PPG waveform morphology is related to the arterial blood pressure waveform. As expected after each premature ventricular beat, there is a compensatory pause, which gives more time for the ventricle to fill. The next normal heartbeat is, therefore, associated with an increase in stroke volume. This is reflected in an increase of arterial blood pressure. It is thought that the same mechanism accounts for an increase in the size of the pulse oximeter amplitude after a compensatory pause. A beat-to-beat change of the pulse oximeter amplitude is often the first clue that the patient has developed an irregular heart rhythm.

Pulse analysis: the analysis and measurement of specific time interval and areas of the PPG waveform provide additional details about the health status of the subject.

Figure 6:
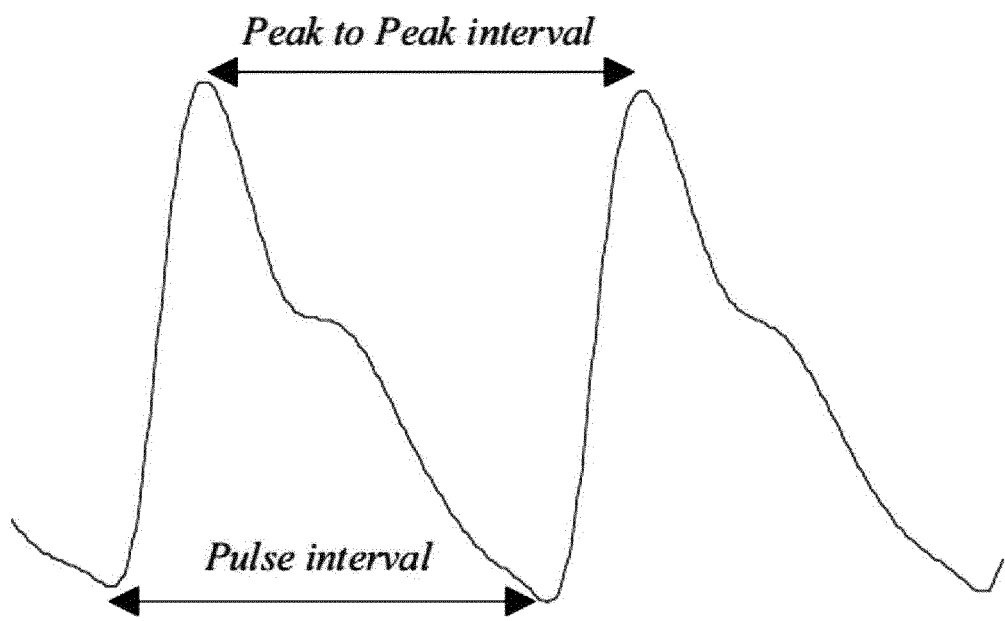
FIG. 6 shows two consecutive PPG waveforms.

As shown in FIG. 6, the distance between two consecutive systolic peaks will be referred to as Peak-Peak interval, which has been used to detect the heart rate in PPG signals.

Moreover, the distance between the beginning and the end of the PPG waveform will be referred to as Pulse interval. The Pulse interval is usually used instead of the Peak-Peak interval when the diastolic peaks are more clear and easier to detect compared to the systolic peak. It has been suggested that ratio of Pulse interval to its systolic amplitude could provide an understanding of the properties of a person's cardiovascular system. It has been demonstrated that Heart Rate Variability (HRV) in PPG and ECG signals are highly correlated: consequently, the PPG signals could be used as an alternative measurement of HRV.

The augmentation pressure is the measure of the contribution that the wave reflection makes to the systolic arterial pressure, and it is obtained by measuring the reflected wave coming from the periphery to the centre. Reduced compliance of the elastic arteries causes an earlier return of the "reflected wave", which arrives in systole rather than in diastole, causing a disproportionate rise in systolic pressure and an increase in pulse pressure, with a consequent increase in left ventricular after load and a decrease in diastolic blood pressure and impaired coronary perfusion.

The augmentation index (AI) is defined as follows: AI=y/x

As shown in FIG. 5, y is the height of the late systolic peak and x is the early systolic peak in the pulse. The systolic component of the waveform arises mainly from a forward-going pressure wave transmitted along a direct path from the left ventricle to the finger. The diastolic component arises mainly from pressure waves transmitted along the aorta to small arteries in the lower body, from where they are then reflected back along the aorta as a reflected wave, which then travels to the finger.

Figure 7:
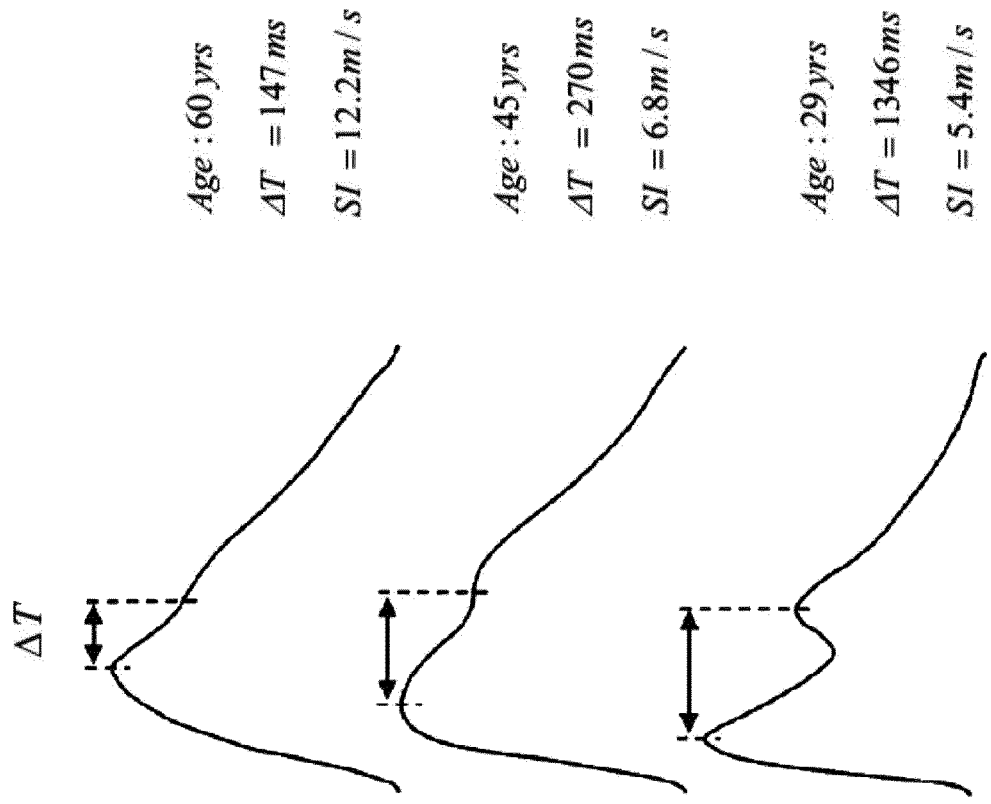
FIG. 7 shows a quantity denoted by $\Delta T$ on a PPG waveform (left) and typical PPG waveforms and associated $\Delta T$ (right).
Figure 7:
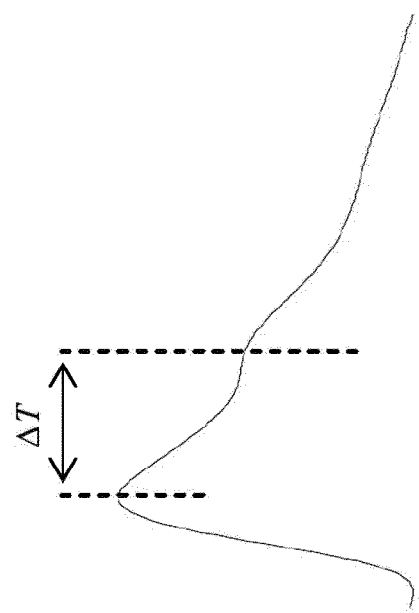

The upper limb provides a common conduit for both the directly transmitted pressure wave and the reflected wave and, therefore, has little influence on their relative timing. As shown in FIG. 7, on the left, the time delay $\Delta T$ between the systolic and diastolic peaks or, in the absence of a second peak, the point of inflection, is related to the transit time of pressure waves from the root of the subclavian artery to the apparent site of reflection and back to the subclavian artery. This path length can be assumed to be proportional to subject height h.

Therefore, an index of the contour of the PPG (SI) that relates to large artery stiffness is defined as SI=h/$\Delta T$.

As shown in FIG. 7, on the right, the time delay between the systolic and diastolic peaks decreases with age as a consequence of increased large artery stiffness and increased pulse wave velocity of pressure waves in the aorta and large arteries. Therefore, it has been proven that the SI increases with age.

Mathematical analysis supports a more refined parameter identification as well as extracting additional features from the PPG waveform. For instance, the first derivative is mainly used to better identify the diastolic point. The second derivative of plethysmograph is also called the acceleration plethysmograph because it is an indicator of the acceleration of the blood in the finger.

Figure 8:
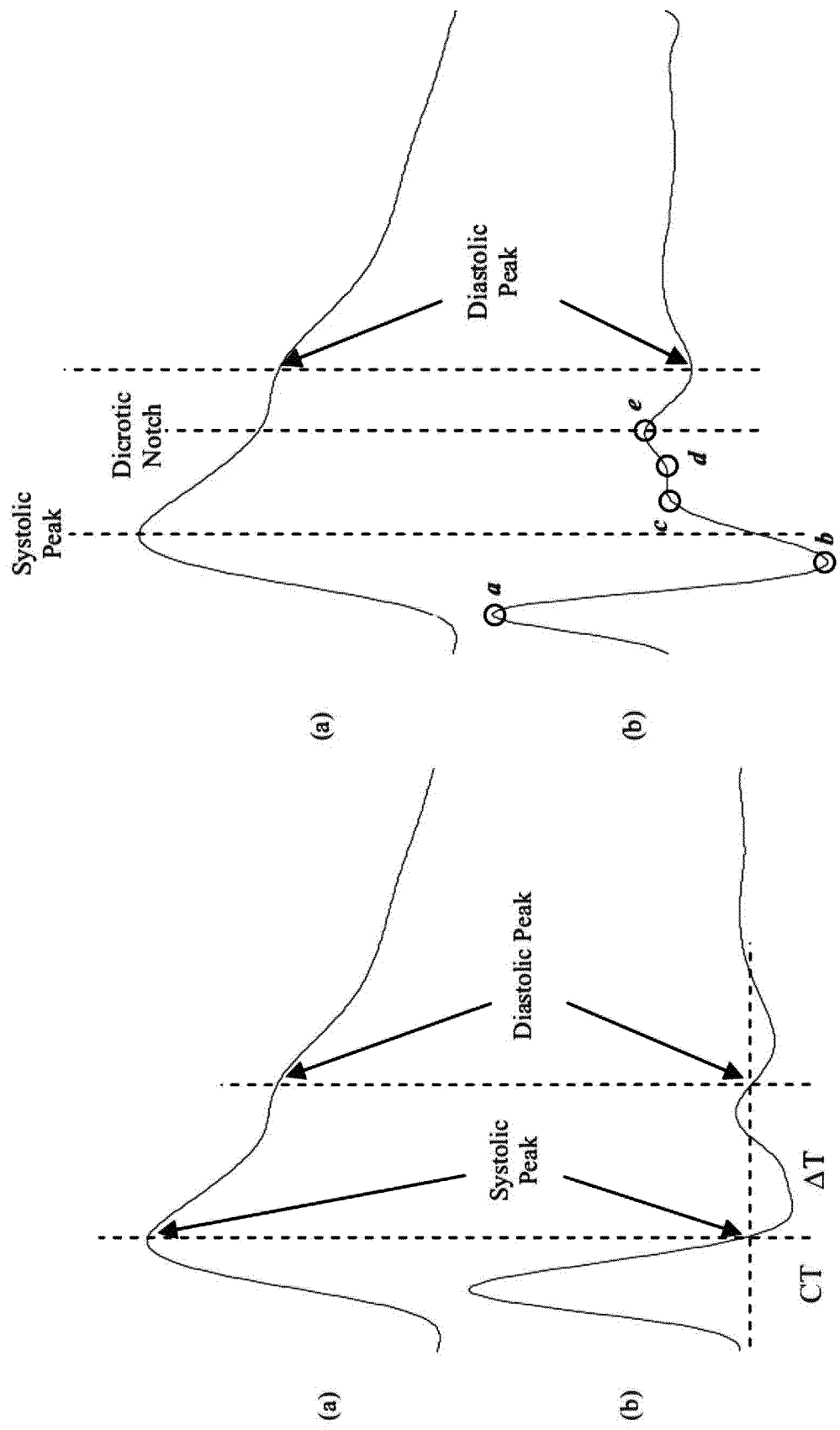
FIG. 8 shows (a) Original fingertip plethysmograph, (b) first derivative wave of plethysmograph (left), and (b) second derivative wave of plethysmograph (right).
Figure 9:
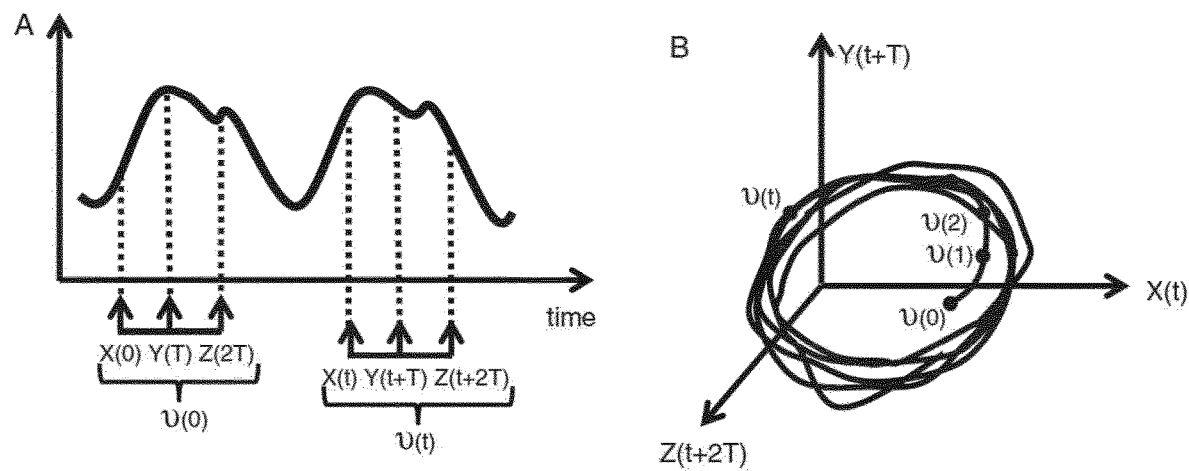
FIG. 9 shows a conceptual scheme of the reconstruction phase from observed nonlinear data.

FIG. 8 shows an original fingertip plethysmograph (a), the first derivative wave of the plethysmograph ((b)—left), and the second derivative wave of plethysmograph ((b)—right).

Autonomic and parasympathetic/sympathetic system activity: the behaviour of the Autonomic Nervous System (ANS) can be studied by means of a frequency domain analysis of the PPG. In particular, the LF band (0.04-0.15 Hz), which includes rhythms with periods between 7 and 25 s and is affected by breathing from ~3 to 9 bpm, and the HF or respiratory band (0.15-0.40 Hz), which is influenced by breathing from 9 to 24 bpm, can be extracted from the PPG. Like HRV, the HF component is an index of parasympathetic nerve activity, and the LF/HF ratio is an index of sympathetic nerve activity.

The single spot monitoring and the need to apply a PPG sensor directly to the skin limit the pulse oximetry applicability in situations such as perfusion mapping and healing assessments or when free movement is required.

Moreover, conventional PPG sensors need to be firmly attached to the skin in order to get an high-quality signal. The introduction of fast digital cameras into clinical imaging monitoring and diagnosis systems as well as very advanced solutions based on ultra-short-range RADAR technology (e.g., 1-3 meters), the desire to reduce the physical restrictions, and the possible new insights that might come from perfusion imaging and mapping inspired the evolution of the conventional PPG technology to Imaging PPG (IPPG).

IPPG is a noncontact method that can detect heart-generated pulse waves by means of peripheral blood perfusion measurements. Since its inception, IPPG has attracted significant public interest and provided opportunities to improve personal healthcare.

Therefore, an IPPG technology is needed to offer detailed spatial information simultaneously from multiple sites of arbitrary sizes and locations, thus, allowing the derivation and mapping of physiological parameters, and ultimately, facilitating insights that would otherwise be difficult or even impossible to obtain from single-point measurements.

For the sake of clarity, an IPPG sensor installed nearby the internal mirror of the vehicle could simultaneously analyse and predict the WDS transition of the driver and the health status of the passenger close to him/her.

In particular, mental stress consists in "a body or mental tension resulting from factors that tend to alter an existing balance": hence, it appears as a natural reaction to an unexpected change and can be also seen as a defensive process to protect a person against possible injuries or treats to emotional well-being. Stress refers to a biological condition of the ANS that allows reaction to a demand or unknown situation. All physiological responses related to stress are controlled in the ANS. The latter is divided into Sympathetic Nervous System (SNS) and Parasympathetic Nervous System (PNS), the former controls activities that are activated during emergency or unknown situations and the latter controls the rest and restoration functions of energy.

Currently there are several technologies and methods available to monitor biological changes which can be associated to stress and emotional status.

One of the most common bio-signal used to detect chronic stress on humans is electro-dermal activity. Human skin can be modelled as electrical conductor: in fact, in case of a cognitive, emotional or physical stressor, skin glands will produce ionic sweat.

In particular Galvanic Skin Reflection is an indicator of electrical Skin Conductivity (SC), as conductivity increases linearly in presence of external or internal stimulus.

Tension in muscles is a common indicator of an external stimulus, consequently it is possible to assess emotional changes using muscular activity-based signals, through Electromyogram. (EMG). EMG uses electrodes on the superficial layers of the muscles to detect electro-activity during muscles fibres contractions, and is a very invasive technique.

A relative new technique to measure stress and emotional changes is by using advanced vision system: for instance, the Hyperspectral Imaging methodology combines oxygen saturation, temperature through contact sensors with facial movements and changes on the eye's pupil in order to detect emotional changes.

Finally, cardiovascular activity refers to any measure that involve hearth and blood vessels: those bio-signals provide a wide range of information regarding different physical and psychological conditions. The cardiovascular activity can be measured in an invasive manner through ECG.

It is important to note that the previous technique to measure stress and emotional changes are either invasive or very complex to be implemented.

Indeed, the amount of blood flowing into the peripheral vessels can be measured quite precisely and in a less-invasive manner using the PPG technology.

Several features, normally chosen for their widespread use in the estimation of the activity of the ANS, can be derived from the PPG in the time domain such as:
1. Average NN is the average time between normal heartbeats. Low values denote an elevated heart rate that could indicate excitement, physical activity and coffee assumption. Higher NN values typically denote resting.
2. SDNN is the standard deviation of the time between heartbeats and can be used to estimate physiological stress.
3. RMSSD is the root mean square of successive differences of heartbeats and it has been used to predict the perceived mental stress.
4. SDSD is the standard deviation of successive differences.
5. NN50 is the number of adjacent NN intervals that differ from each other by more than 50 ms (NN50) and requires a 2 min epoch. The proportion term pNN50 is NN50 divided by the total number of NNs. A high percentage indicates complexity in heart rate variability, correlated with good psychological and physiological state.

Additional indexes can be extracted from the PPG, through more complicated processing such as the chaotic attractor and the largest Lyapunov exponent.

A first step in nonlinear time analysis, is the reconstruction of the phase space, which is an abstract mathematical space where the chaos can be observed, from PPG data. A reconstructed phase can be described as follows:

$$v(t)=[X(t),Y(t+T),Z(t+(d-1)T]$$

In particular, v(t) is the dimensional state vector, X, Y and Z are original data, d is the number of embedded dimensions, and T is the time delay. An appropriate time delay T and embedded dimension d are important for reconstructing the attractor.

Since the attractor is derived from the PPG, the relative size of the attractor reflects the PPG amplitude. If the peripheral blood flow decreased, the size of the attractor decreased. The shape of the attractor is formed by the trajectory and describes the instability of the PPG wave, which is correlated with the chaos status. If the level of chaos increases, the chaotic attractor tends towards a very irregular shape.

Figure 1A:
FIGS. 1A and 1B show assembly of a polysomnography on a patient and display on a personal computer of the recorded signals, respectively.
Figure 1B:
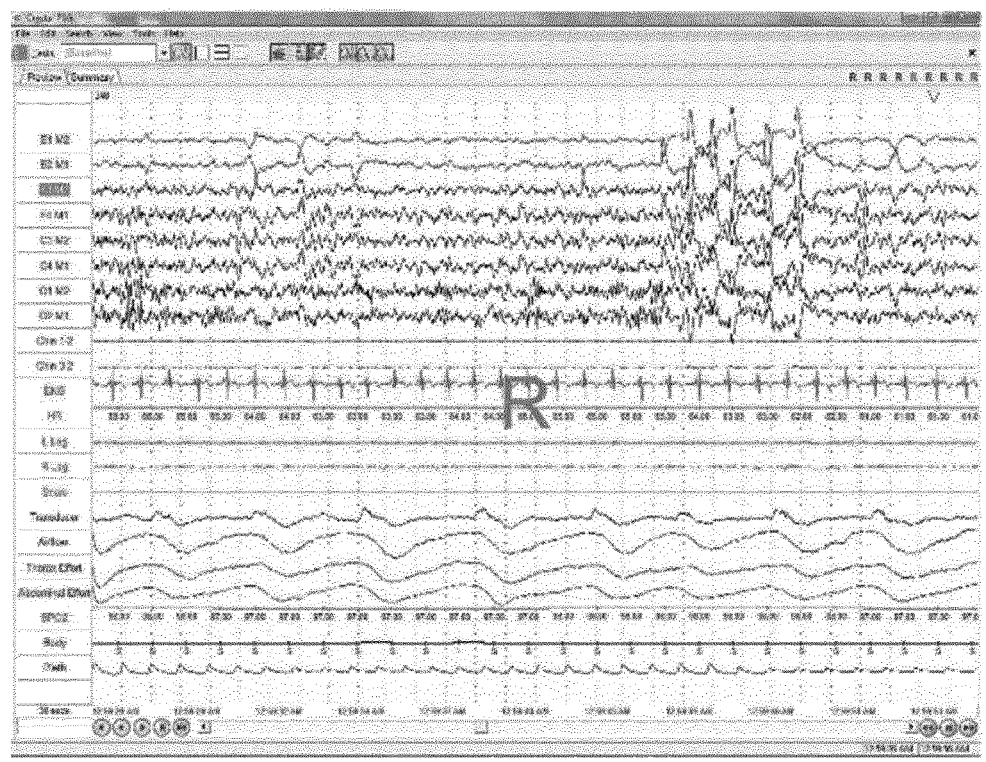
Figure 2:
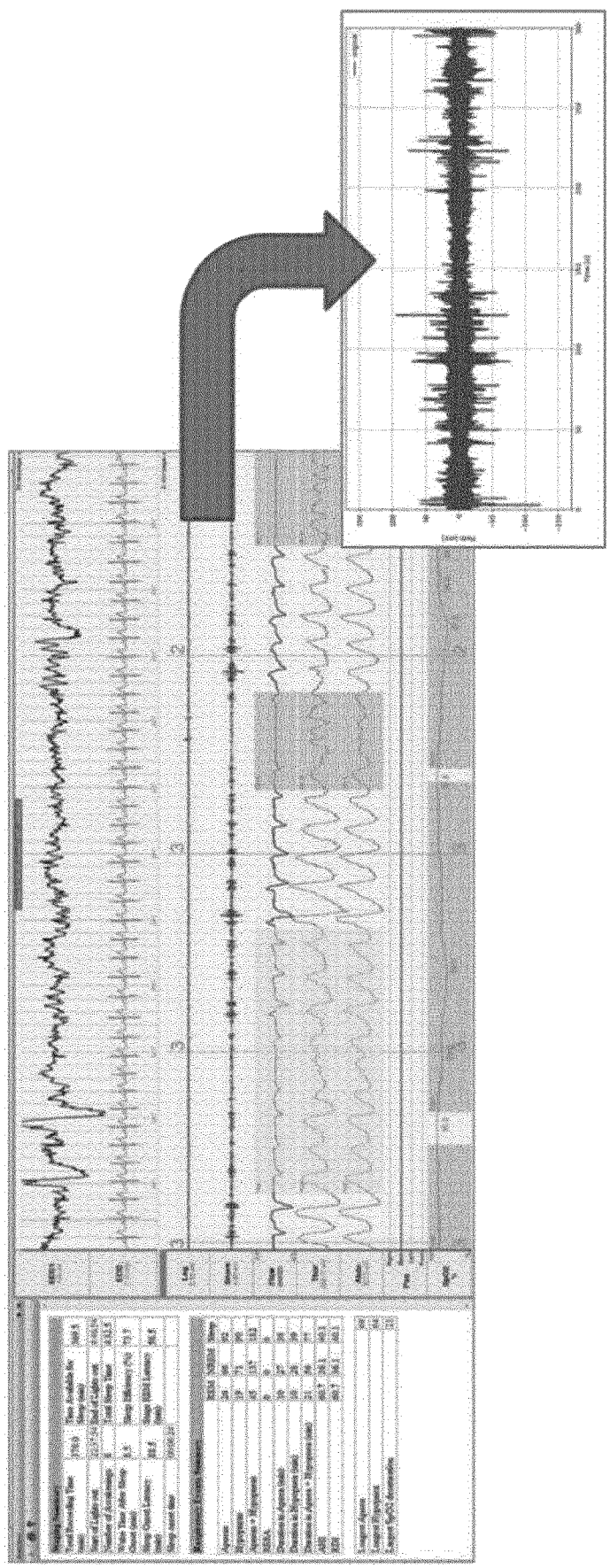
FIG. 2 summarizes the idea underlying the present invention based on multi-factors extracted through PPG technology.

FIG. 2 shows a conceptual scheme of the reconstruction phase from observed nonlinear data.

The Lyapunov exponent of a dynamical system is a quantity that characterizes the rate of separation of adjacent trajectories. The rate of separation can be different for different orientations of the initial separation vector. Thus, there is a spectrum of Lyapunov exponents, equal in number to the dimensionality of the phase space. It is common to refer to the largest one as the Maximal Lyapunov Exponent (MLE), because it determines a notion of predictability for a dynamical system. The MLE, which quantitatively shows the level of chaos, is extracted from the attractor. In particular the MLE is calculated with the Rosenstein's algorithm: such a method follows directly from the definition of the largest MLE and is accurate because it takes advantage of all the available data. The Rosenstein's algorithm is fast, easy to implement, and robust to changes in the following quantities: embedding dimension, size of data set, reconstruction delay, and noise level.

An increase in the MLE signifies that the irregularity of the level of chaos has increased. Generally, when healthy people have mental stress and try to overcome difficulties, the level of chaos will increase.

Therefore, PPG can be one of the most effective methods to evaluate mental stress quantitatively. Worthy to note that a combination of time domain and frequency domain seems to be the most appropriate approach to achieve reliable indications about stress.

The term "somnificity" has been introduced some years ago to describe the effects of different postures and activities on sleep propensity.

In particular, the somnificity of any particular posture, activity and situation is a measure of its ability to facilitate or impede sleep onset in the majority of people. It is not a characteristic of individual people or their sleep disorders.

A person's usual sleep propensity when engaged in the same activity repeatedly (in the same posture and at the same time of day, etc.) can be referred as the Situational Sleep Propensity (SSP) in that situation. When we measure a person's sleep propensity under one set of circumstances, e.g. by how long it takes them to fall asleep at two hourly intervals during the day in a sleep laboratory (the Multiple Sleep Latency Test) we are measuring only one of their SSPs. This is usually quite different from their sleep propensity measured under different circumstances, e.g. by how long it takes them to fall asleep in the Maintenance of Wakefulness Test. A person's SSP in one situation is usually moderately correlated with their SSP in a different situation.

In particular, the time horizon of the falling asleep event is certainly influenced also by the emotional phase and the stress level. Even in the same boundary conditions (e.g. posture, location, time of the day) and behavioural conditions (e.g. fatigue level, general health status) the presence/absence of any mental stress on the subject can directly affect the sleep onset.

An aspect of the proposed methodology is about having a very comprehensive analysis of the Situational Sleep Propensity taking into account multiple behavioural factors extracted through PPG technology, as previously described, and analysing them in multiple-domains (e.g. time and frequency).

Figure 10:
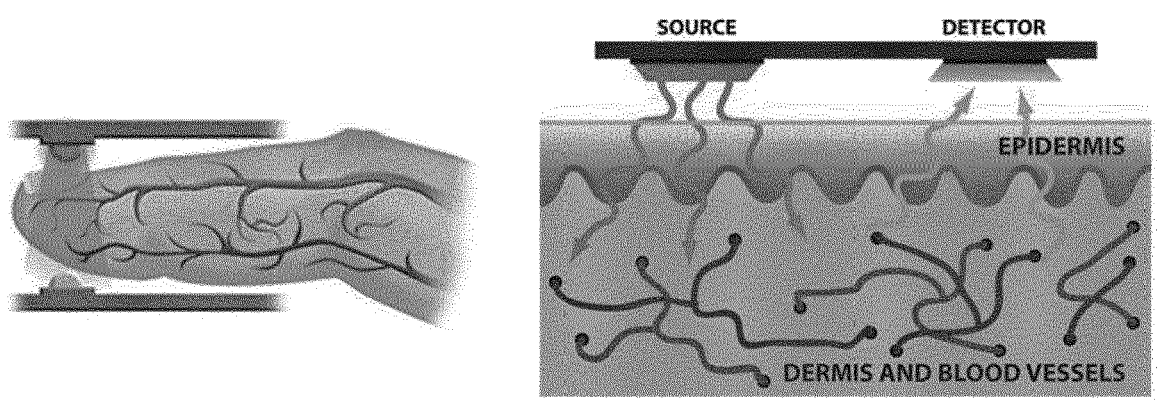
FIG. 10 shows PPG transmission (left) and reflection (right) modes.

In particular, the proposed W-D-S detection and prediction methodology is based upon some fundamental physics and medical observations:

1. the PPG waveform is characterized by an irregular trend during the Awake phase and a regular trend during the sleep phase, while in the drowsiness phase the PPG waveform progressively tends towards a regular trend. This phenomenon can be observed both in terms of frequency values as well as in terms of amplitude values, as described in more details below;
2. the heart rate varies between the Awake phase and the sleep phase;
3. the energy delivered on each measuring pulse in the PPG technology can be substantially considered constant, since the optical source is driven with a constant driving current. This statement is independent from the contact PPG technology (e.g., PPG transmission (left) and reflection (right) modes, as shown in FIG. 10). The same principle holds in the case of IPPG technology, since either the short-range RADAR or an equivalent technology produce a constant beam for the physiological analysis.

In the previous section, several relevant parameters regarding the health status of the subject have been described. Those parameters can be mainly extracted through a time domain analysis and could provide very useful information about W-D-S phases.

However, it must be underlined that the quality of PPG waveform is normally low and it is prone both to artefact due to wrist movement and noise due to external light. Consequently, it is not easy to obtain very detailed information from the PPG unless applying rather heavy filtering to remove noise. It is also difficult to implement very selective real-time filtering on cost sensitive embedded systems. Hence heavy filtering remove not only noise but also useful information contained within the PPG signal. For those reasons, time-based algorithms might not be very accurate and are difficult to be calibrated.

The rationale behind the use of PPG features for detection/prediction of W-D-S phases is the following. W-D-S phases differ from each other not only from the behavioural and cognitive point of view, but also from the cardiovascular, respiratory and autonomic ones. Awake state is characterized by an increase in sympathetic activity and/or a decrease of parasympathetic activity, while extreme relaxation states and sleep state are characterized by an increase in parasympathetic activity and/or a decrease in sympathetic activity. Therefore, since the PPG signal is a biomedical variable related to the autonomic nervous system, it can provide direct information of individual physiological state (W, D, S) in a simple and non-invasive way.

In fact, recent studies have shown that amplitude changes of the PPG waveform observed in PSG recordings are associated with activations of the cerebral cortex. These activations are characteristic for example of the episodes of short awakenings (arousals) that occur after a respiratory event of sleep. This suggests that changes in the PPG wave could be considered as markers of awake cortical activity.

Moreover, PPG is sensitive to body movements typical of Awake state that cause a remarkable variability of the waveform. The sensibility of the PPG waveform to body movements is a well-known characteristic of this signal and it is usually considered one of its limits because it generates a "noise" that disturbs the analysis of the wave and the correct extraction from it of some information such as, first of all, oxygen saturation and heart rate values. At the same time, however, the observation of a prolonged irregularity of the wave caused by the movement provides information about the behavioural state of the subject and it is suggestive of a awake phase.

Therefore, PPG waveform is characterized by an irregular trend during the Awake phase and a regular trend during the sleep phase. The trend of the PPG waveform (AC and DC components) in the awake and sleep phases is shown in FIG. 11, both in a rather detailed window period (above) and in a large window scale (below).

Figure 11:
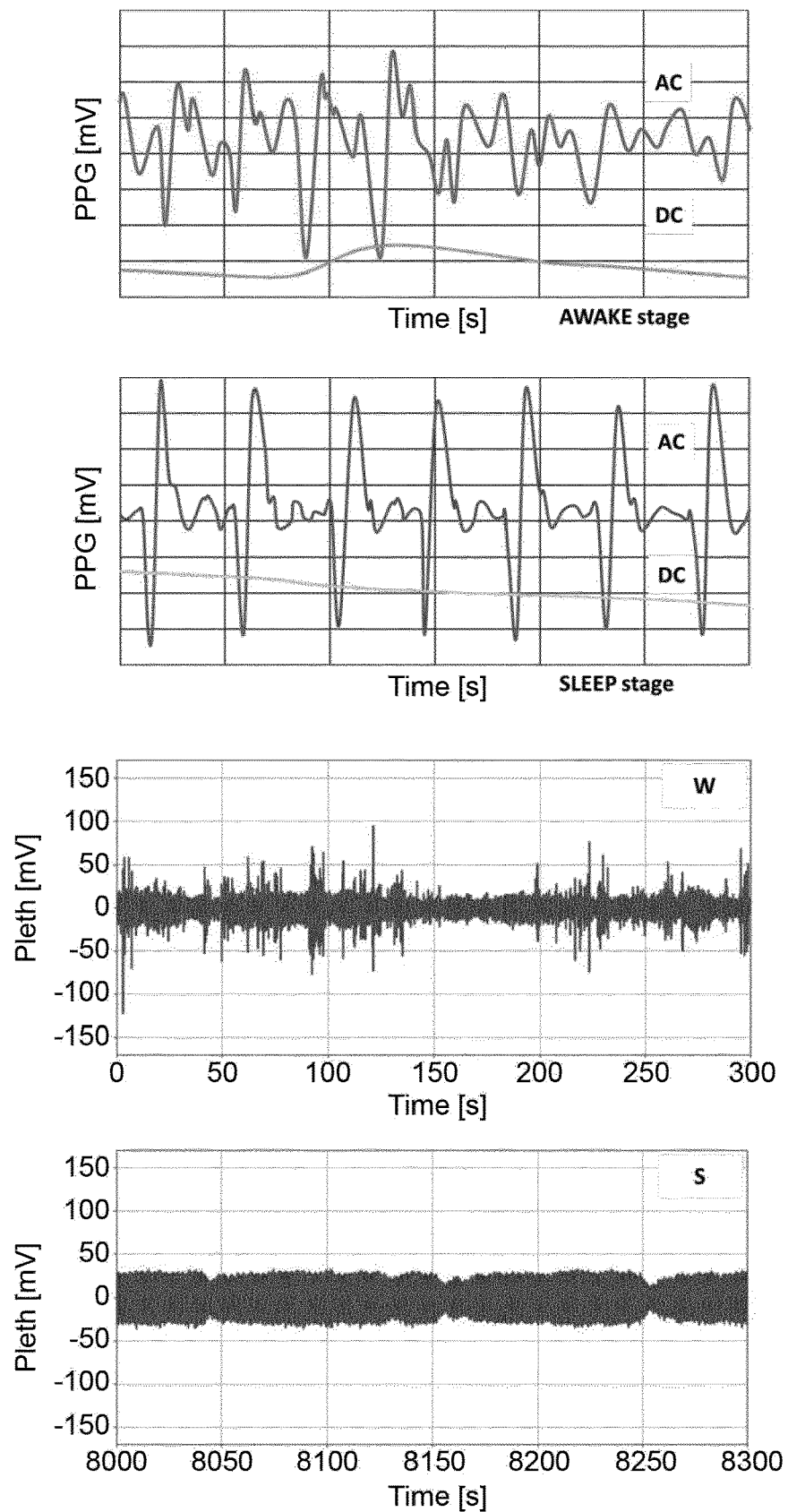
FIG. 11 shows trends of a PPG signal (AC and DC components) in awake and sleep phases.

In particular, the PPG waveforms shown in FIG. 11 describe the behaviour of the subject 10 minutes before sleeping and 10 minutes after sleeping.

The drowsiness condition is the transition process between W and S that precedes the sleep phase. It is further complicated by the fact that sleep onset does not occur all at once and some fluctuations in vigilance may occur before reaching a stable condition.

In the drowsiness phase, the PPG waveform progressively tends towards a regular trend.

This fundamental conclusion is the result of accurate and exhaustive clinical observations carried out by experts in the field of sleep medicine over a large period of time.

Different behaviour phases have been analysed by medical doctors expert in sleep medicine based on the recommendations of the AASM (American Academy of Sleep Medicine) for sleep scoring. The following states have been scored:
 a) NonREM 1-2-3 and REM sleep phases
 b) Movements during sleep
 c) Waking state In addition, the waking phase have been further differentiated into active, quiet and quiet with eyes closed in order to better define the transition between Awake and sleep phases.

A proprietary database, including high resolution physiological data acquired through the PSG methodology, which represents the gold standard of sleep studies has been built. The database includes the epochs relating to all the transitions of behavioural status reported on a table (expressed in hours, minutes and seconds). Such a table has been used for the development and the validation of the detection/prediction algorithm.

Worthy to mention the activity performed about sleep-related breathing disorders where it was important to look at some physiological parameters (e.g., from sleep to Awake phase) in order to identify sudden arousal events caused by apnoea.

Hence, there are different features of the physiological parameters between sleep and Awake phases, with particular respect to the PPG waveform trend.

The opposite is also true when the observation is focused on the transition between W and S phases.

Figure 12:
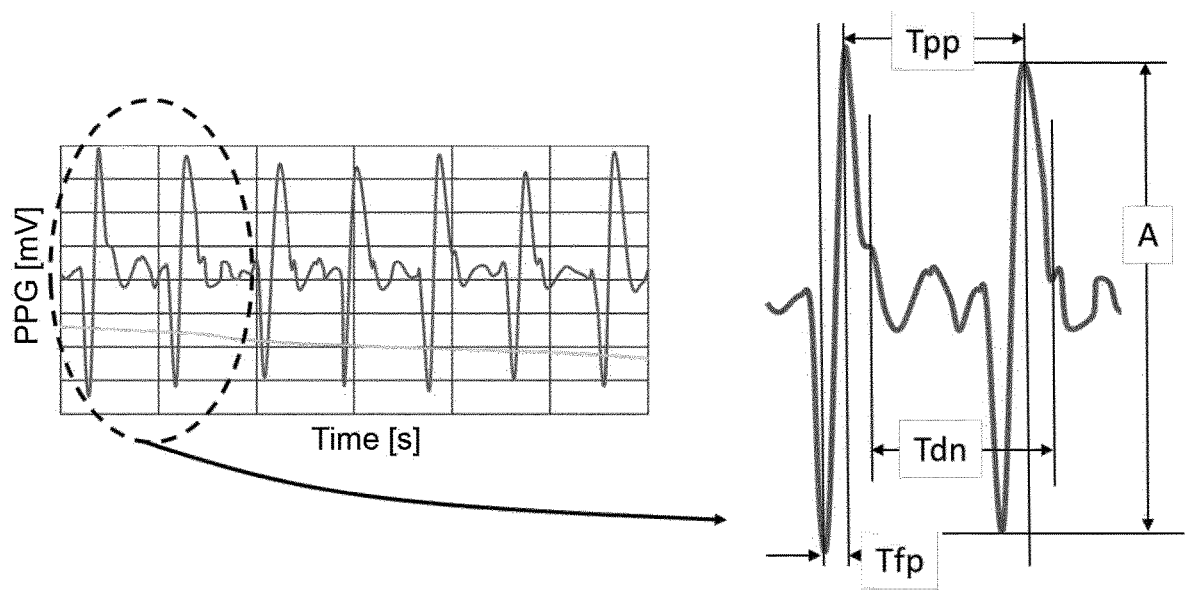
FIG. 12 shows quantities Tpp, Tfp, Tdn, and A used in the analysis of a PPG waveform.

Consequently, the visual evaluation performed by medical doctors, according to AASM recommendations, headed to the identification of some relevant signatures of the PPG waveform in the transition phases between W and S phase, such as:
 a) significant reduction in waveform frequency and amplitude variability
 b) significant reduction in motion artefacts frequency FIG. 12 shows some useful quantities used in the time-based analysis of a PPG waveform:
 1. Tpp: time between adjacent peaks of the pulse
 2. Tfp: time between adjacent foot and peak of the pulse
 3. Tdn: time between adjacent dicrotic notches of the pulse
 4. A: peak to peak amplitude of the pulse It is important to note that the above-mentioned reduction in the physiological parameters, visually identified by the medical doctors, is to be considered as a relative change for the subject under analysis and not as an absolute index. Therefore, suitable "signature windows", peculiar to each subject and changing over time according to his/her health status, can be defined and used to detect the transition from W and S phases.

Consequently, it has been possible to deal with a very limited number of physiological parameters, extracted only through PPG technology, which include all the needed signatures to detect the drowsiness condition, and more generally the W-D-S transitions, with high accuracy.

Such a scientific approach, which has been clinically verified, could lead to the identification of a robust method for the detection of the W-D-S phases.

Most of the scientific activities have been focused, so far, on the detection of the different sleep phases but without looking at the W-S transition based only on the PPG technology.

With regard to the analysis in the time domain, it is focused on maximum peaks to search for regularity variation. It is based either on general peaks behaviour or difference between consecutive peaks, according to the experimental activity performed by clinicians on a relevant data-set of physiological values describing the W-D-S transitions.

The following representative features in the time domain have been identified: MaxPeaks_95perc: it is the absolute value of difference between the maximum and the 95% percentile of amplitude of peaks:

$$\text{MaxPeaks\_95}_{perc} = |\max(\text{peaks}) - p_{95}(\text{peaks})|$$

Outliers: it is the percentage of peaks out of the range centred on the mean of peaks +/−10%

$$\text{Outliers} = \frac{\# \text{peaks} \notin [(1-0.1)\cdot\overline{\text{peaks}}, (1+0.1)\cdot\overline{\text{peaks}}]}{\text{length (peaks)}}$$

Figure 13:
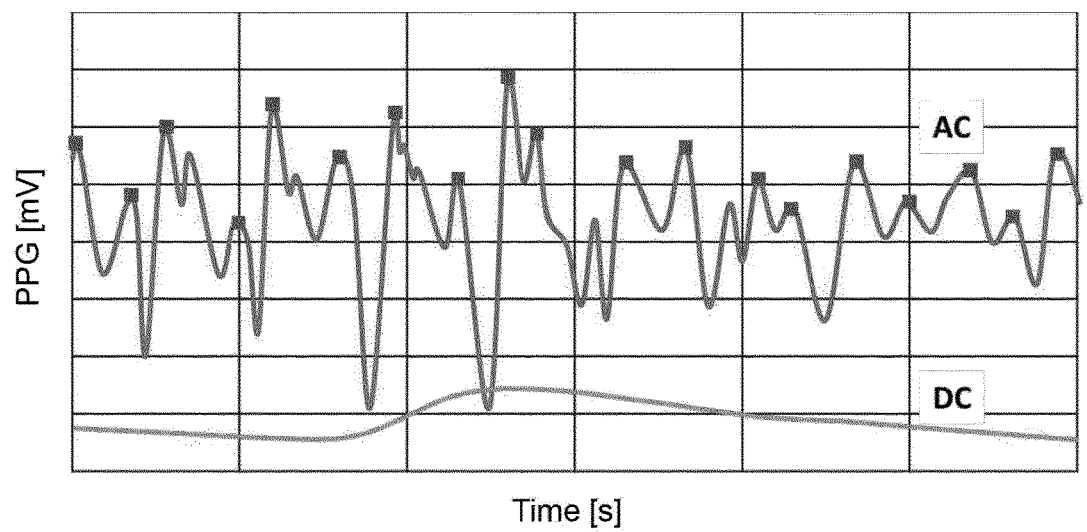
FIG. 13 shows quantities MaxPeaks_95perc and Outlier computed on a PPG waveform.

Searching for consecutive peaks in the PPG waveform and computing MaxPeaks_95perc and Outliers is shown in FIG. 13.

Additionally, the following parameters defined by the Task Force of the European Society of Cardiology and the North American Society of Pacing and Electrophysiology, and previously described in relation to the emotional phases, are computed (the calibratable measurement time epoch is between 2 and 5 min):
 1. Average NN: average time between normal heartbeats in [ms]
 2. SDNN: standard deviation of the time between heartbeats in [ms]
 3. RMSSD: root mean square of successive differences of heartbeats in [ms]
 4. SDSD: standard deviation of successive differences in [ms]
 5. NN50: number of adjacent NN intervals that differ from each other by more than 50 ms The Largest Lyapunov Exponent with Rosenstein's Algorithm is currently available as a MATLAB library function and the SW code may be tailored to the selected CPS platform.

With regard to the analysis in the frequency domain, it has been rarely used in PPG technology due to the fact it is much less intuitive for clinicians to assess the results of the measurement. Moreover, it wasn't easy to implement real-time frequency analysis on the previous generation of biomedical portable systems due to the lack of processing capabilities and embedded memory.

The PPG technology provides a continuous waveform in the time domain. Such a waveform can be described by the sum of infinite number of sinusoidal waves, with defined frequency and amplitude, through the Fourier transformation as follows:

$$X(f)=\int_{-\infty}^{\infty}x(t)e^{-i2\pi ft}dt$$

Through the Fourier Transform any physical signal can be decomposed into a number of discrete frequencies, or a spectrum of frequencies over a continuous range. Starting from the spectrum of the signal x(t) it is possible to calculate the energy spectral density and the power spectrum.

The frequency analysis on the PPG waveform provides details about the spectral content of the waveform in terms of fundamental frequency and main harmonics.

In particular, it has been clearly demonstrated the precise correlation between the heart rate and the fundamental PPG frequency obtained through FFT. By applying the Fourier transform to PPG waveform the spectral distribution can be computed.

Figure 14:
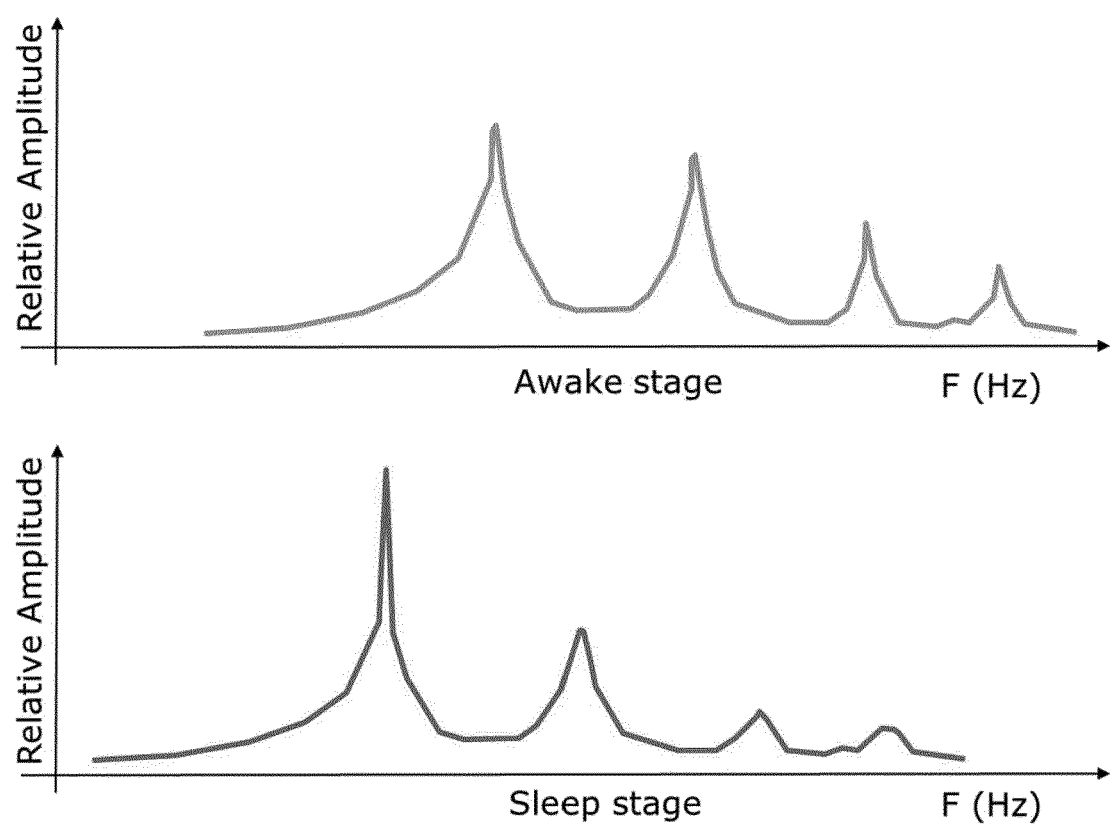
FIG. 14 shows an FFT analysis derived from PPG: awake and sleep phase signal characteristics.

FIG. 14 shows the spectral distributions in both the awake (above) and the sleep (below) phases.

During the W phase the PPG waveform is highly variable, both in terms of frequency and amplitude while in the S phase tends to be much more regular. Looking into the frequency domain, during the W phase, a wide range of harmonics are present; moreover, the main frequencies (e.g. fundamental and first harmonics) have comparable amplitudes. Instead, during the S phase, the fundamental frequency clearly displays a higher relative amplitude with respect to the other harmonics, which are much less pronounced.

Another important consideration is also related the spectrum frequency shift, during the transition from the W to S phase, towards lower frequency range. Worthy to note the way in which energy spreads between the two phases; in particular, a kind of energy re-distribution is observed in the sleep phase, as if more energy were concentrated in the fundamental frequency.

The shift of the fundamental frequency is explained with the reduction of the heart rate in the S phase when compared to the W phase.

Figure 15:
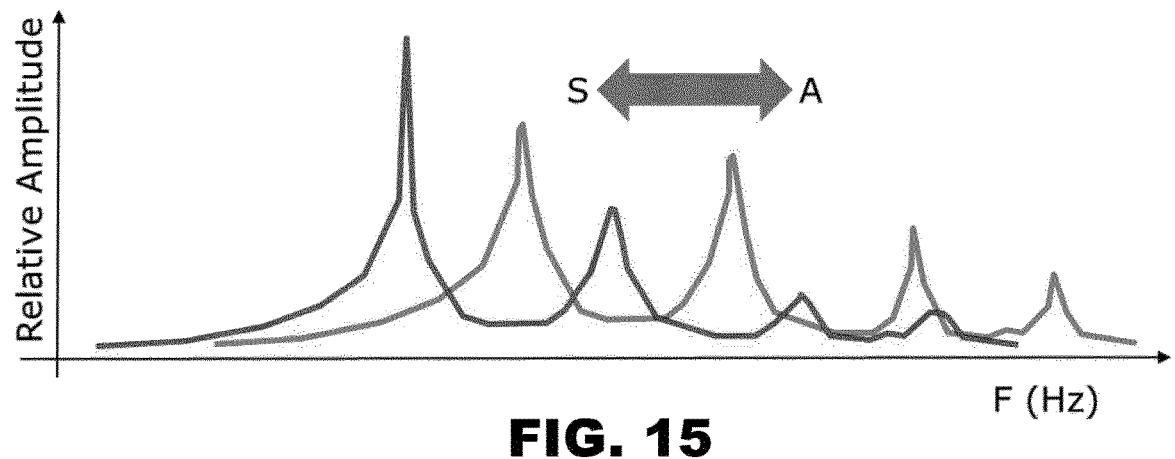
FIG. 15 shows changes in the FFT from W to S phases.

The changes in the FFT from W to S phases, in particular the frequency shift from higher (W) towards lower (S) frequencies, as well as the difference in relative amplitude between the fundamental frequency and the other harmonics are shown in FIG. 15.

Figure 16:
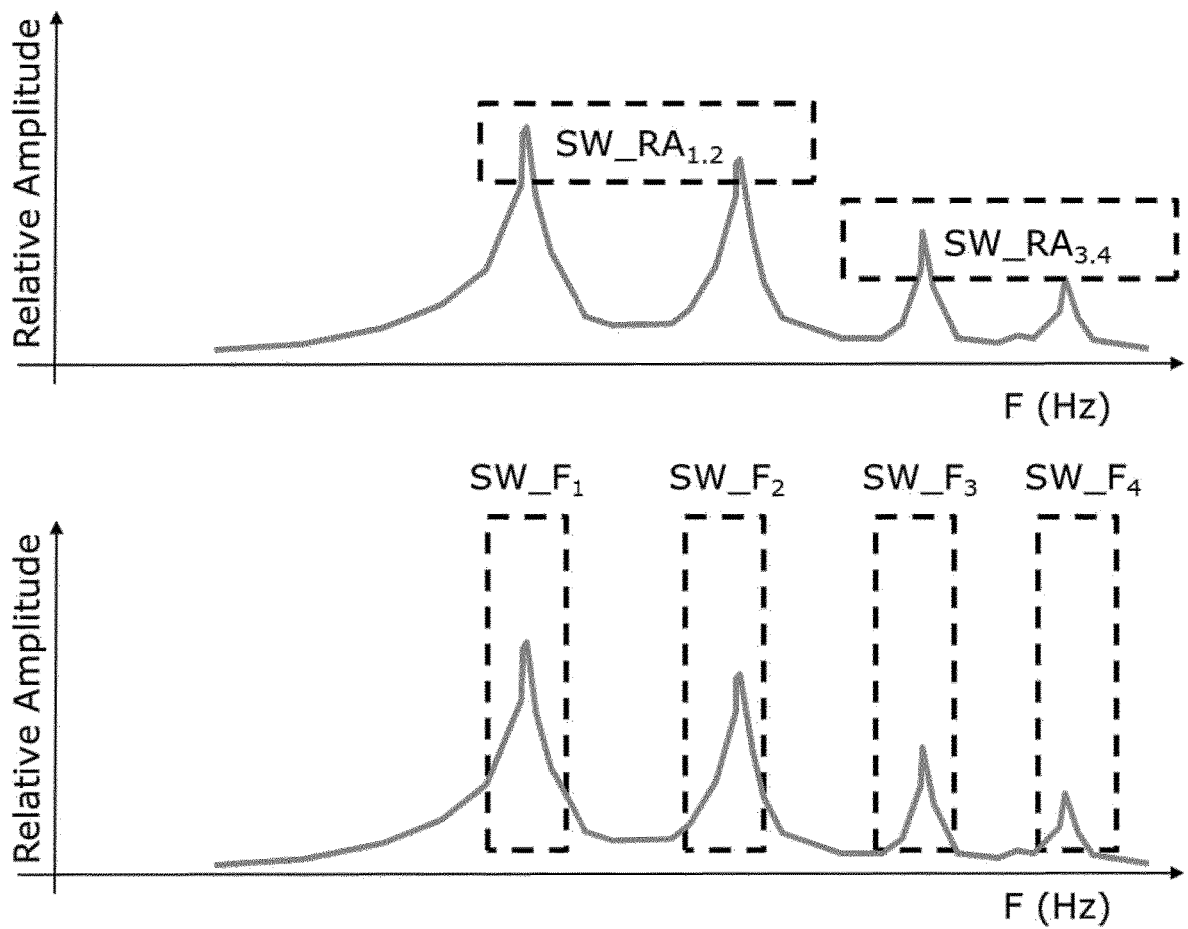
FIG. 16 shows sliding windows both on relative amplitudes and on adjacent frequencies

Hence, it is possible to detect awake and sleep phase thanks to the previous observation. In particular, a set of sliding windows both on adjacent frequencies and on relative amplitudes will provide a dynamic indication about the behavioural phase of the subject (see FIG. 16).

Figure 17:
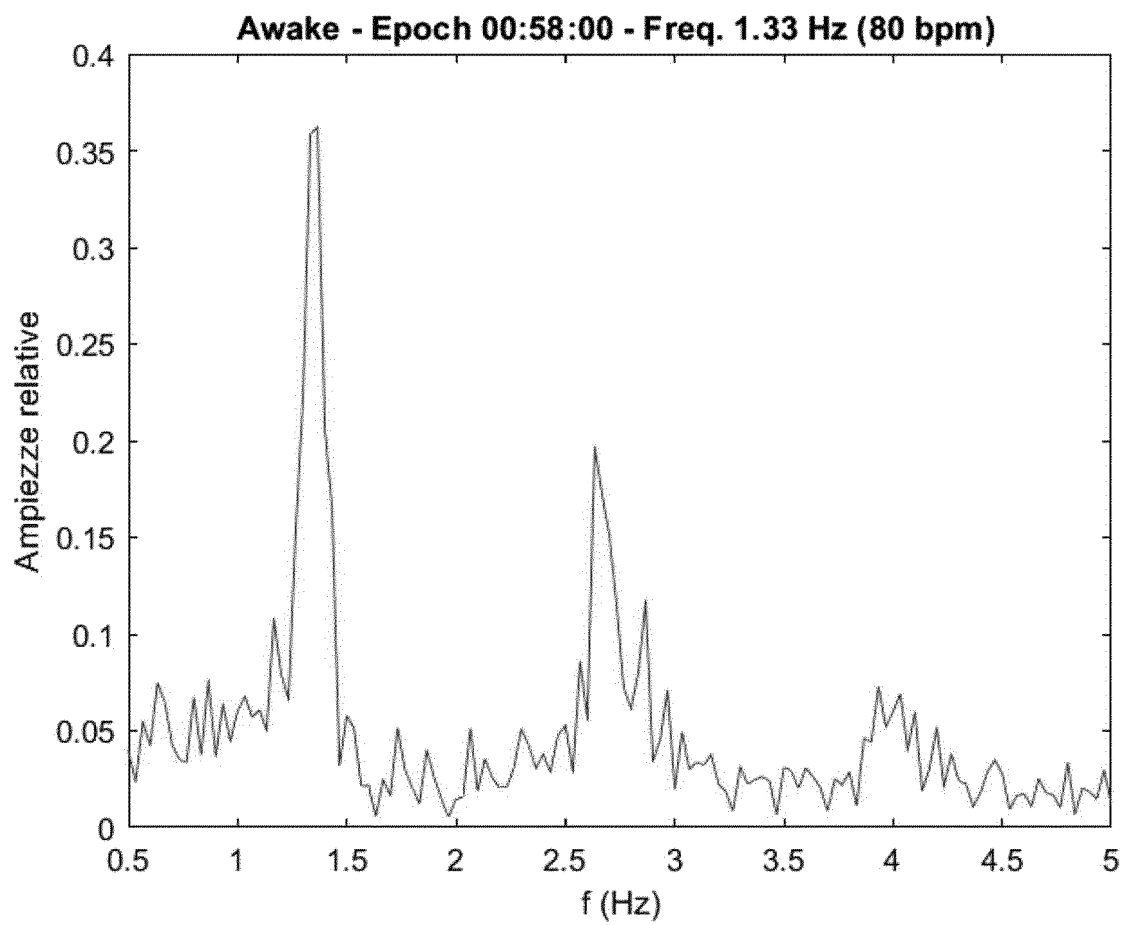
FIG. 17 shows a frequency analysis of a PPG waveform in awake condition.
Figure 18:
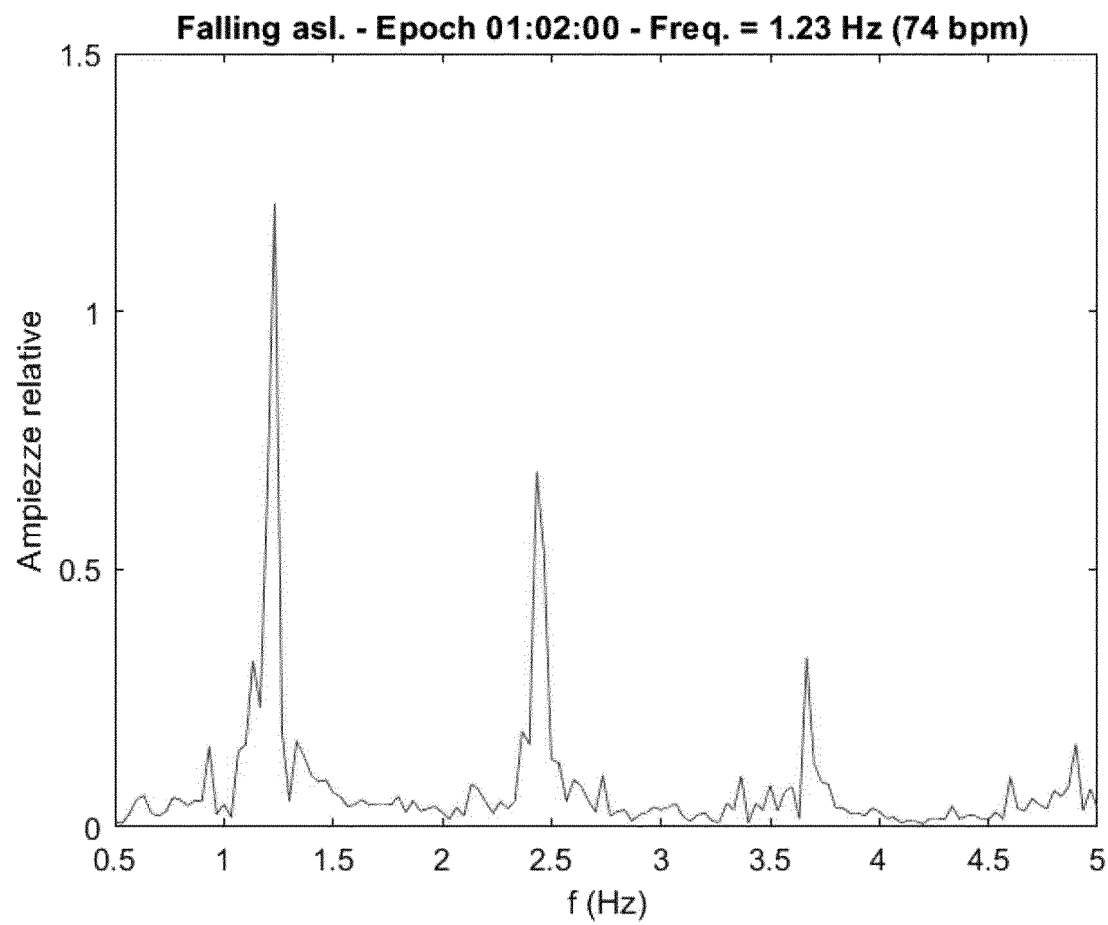
FIG. 18 shows a frequency analysis of a PPG waveform during a falling asleep status.
Figure 19:
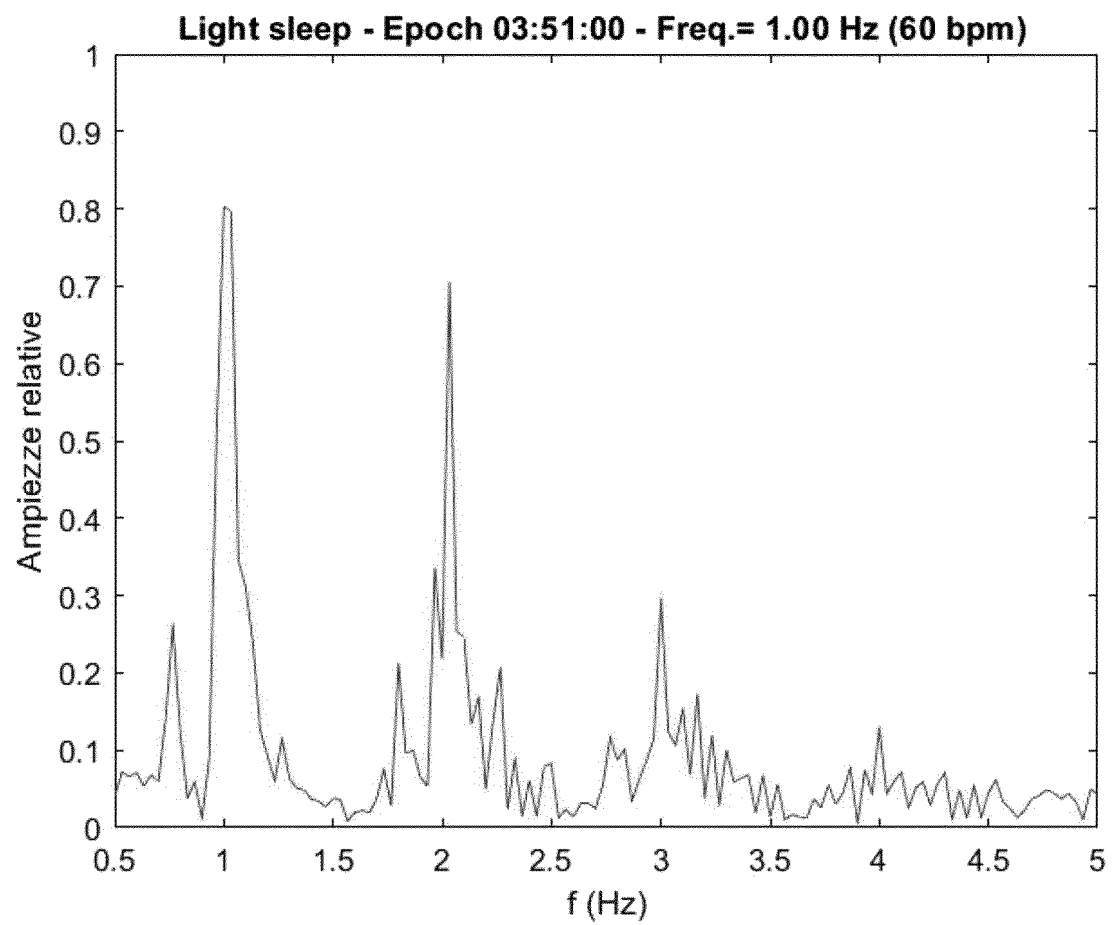
FIG. 19 shows a frequency analysis of a PPG waveform in light sleep status.

Experimental evidence of the previous consideration is provided herein below, which is derived from the proprietary data base. In particular a recording, under controlled conditions, through a biomedical device was performed on a certain amount, considered statistically significant, of subjects for about 10 hours. The test started when the individual was awake and continued for a whole night. Then also the falling asleep and the sleep phases where recorded (including arousals episodes). FIGS. 17, 18, and 19 show the results of the analysis in the frequency domain of the PPG waveform, of a young human being in good health conditions, performed on sliding windows of 30 seconds and classified by sleep medicine experts as awake, falling asleep, and light sleep conditions.

Figure 20:
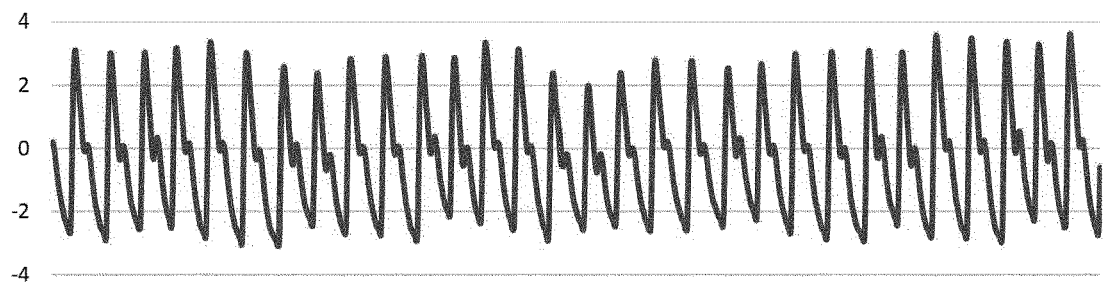
FIG. 20 shows a time domain analysis of a PPG waveform in light sleep status.
Figure 21:
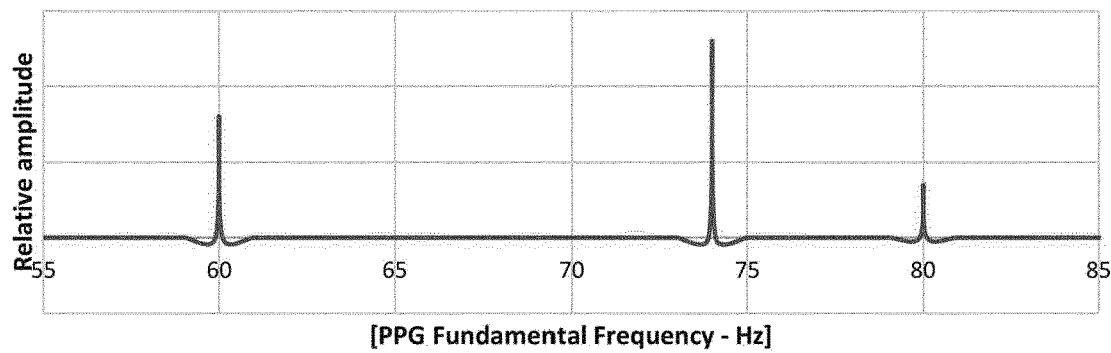
FIG. 21 shows a frequency positioning during test (awake, falling asleep, light sleep).

For the sake of clarity, the representation of the PPG data, in the light sleep status, in the time domain is reported in the FIG. 20, while the frequency positioning of the fundamental frequency only is shown the FIG. 21.

Worthy to mention the correlation between the action of the ANS and the sleep phases.

The non-REM (Rapid Eyes Movement) phase is characterized by a high activity of the parasympathetic system, while the REM and the wake state are characterized by a high activity of the sympathetic one.

Figure 22:
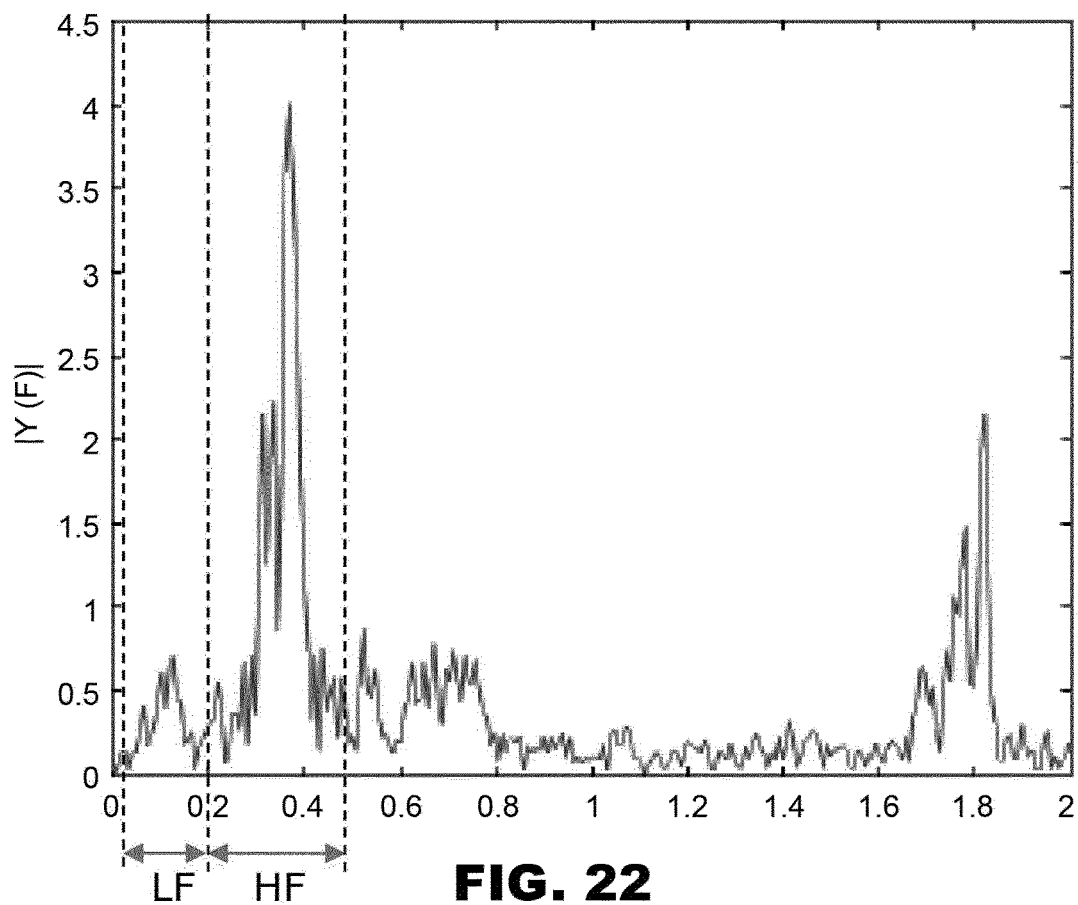
FIG. 22 shows an FFT-based Power Spectrum Density (PSD) of a PPG signal.

Physiological parameters extracted with PPG technology are used to monitor the activity of the sympathetic and the parasympathetic nervous system: such an accurate study is performed in the frequency-domain In particular, the Fast Fourier Transform-based Power Spectrum Density (PSD) of PPG may be computed and is shown in FIG. 22. It can be subdivided into two frequency ranges:
1) Low frequency range (0.04÷0.15 Hz);
2) High frequency range (0.15÷0.4 Hz).

The maximum value in the low frequency range is defined as LF, while the maximum value in the high frequency range is defined as HF.

There is a very important correlation between the action of the automatic nervous system and the HF, LF parameters:
a) when there is an enhancement of the action of the sympathetic nervous system, the value of LF grows up over time.
b) when there is an enhancement of the action of the parasympathetic nervous system, the value of HF grows up over time.

Consequently, the LF/HF ratio, namely k, may be computed:

$$\lambda = \frac{LF}{HF}$$

Due to the relationship between the automatic nervous system and k, sleep phases can be studied as follows:
a) the value of λ increases during the awake state.
b) the value of λ decreases down during the falling asleep state.

By analysing the behaviour of λ over time, for instance through its derivative, it is possible to identify precisely sleep phases and predict the sleep onset safely before the subject could lose his/her level of attention.

The proposed real-time, multi-factor, and multi-domain analysis is the synergic combination of multiple factors, extracted with the PPG technology, and computed either in the frequency domain or in the time domain.

In particular, the fundamental frequency and the first harmonics, the relative amplitude windows as well as the λ are computed in the frequency domain, while additional waveform features, e.g., MaxPeaks_95perc and Outliers, the emotional phase indexes, e.g., average NN, SDNN, RMSSD, SDSD, and NN50, and the Largest Lyapunov Exponent with Rosenstein's Algorithm are computed in the time domain.

It is worthy to mention that the analysis in the time domain relies on the fundamental medical observation previously described: in fact, the PPG waveform is characterized by an irregular trend during the awake phase and a regular trend during the sleep phase, while in the drowsiness phase the PPG waveform progressively tends towards a regular trend. On the basis of this observation the above-mentioned features are computed for: 1) the assessment of the emotional states (e.g. anxiety, relaxation, etc., 2) the prediction of the transition from W to S.

In particular, the peak to peak variation, both in terms of time duration and amplitude, is analysed in real time. Hence relevant variations in time and amplitude of the PPG(t) signal is observed during the W state, while an almost steady state condition, in time and amplitude of the PPG(t) signal is observed during the S state. The analysis of the derivative of those variation, in time and amplitude of the PPG(t) signal is, for instance, a reliable indicator of the behavioural trend of the subject towards a drowsy state. The reference values of the peak to peak variation, in time and amplitude of the PPG(t) signal, are calculated during the learning process thus identifying precisely the W and S phases.

It is important to underline that such a combined analysis on both the time and frequency domain greatly improves the accuracy of the prediction of the behavioural state transition despite the poor quality of the PPG signal.

The comprehensive analysis described so far is complemented and validated through further context details, relative to actual body position and generic health status of the subject, such as:

a) 3 axes wrist accelerations and gyroscope;
b) ambient light level;
c) humidity and temperature measured on the wrist (for PPG sensor calibration).

The multi-axes acceleration on the wrist provides information about the movement of the subject: from one side supports the artefact removal, from the other side informs that the subject is, most likely, awake. The information about temperature, humidity, and ambient light level are used for PPG sensor calibration.

The methodology relies on learning techniques in order to predict the transition from W to S phases. The following Learning and Adaptive control Matrix (LAM) containing frequencies (F) and relative amplitudes (RA) is defined:

| # | Fundamental | $1^{st}$ Harmonic | $2^{nd}$ Harmonic | 3rd Harmonic | 4th Harmonic |
|---|---|---|---|---|---|
| 1 | $f_f(\#1) = (F, RA)$ | $f_1(\#1) = (F, RA)$ | $f_2(\#1) = (F, RA)$ | $f_3(\#1) = (F, RA)$ | $f_4(\#1) = (F, RA)$ |
| 2 | $f_f(\#2) = (F, RA)$ | $f_1(\#2) = (F, RA)$ | $f_2(\#2) = (F, RA)$ | $f_3(\#2) = (F, RA)$ | $f_4(\#2) = (F, RA)$ |
| ... | ... | ... | ... | ... | ... |
| k | $f_f(\#k) = (F, RA)$ | $f_1(\#k) = (F, RA)$ | $f_2(\#k) = (F, RA)$ | $f_3(\#k) = (F, RA)$ | $f_4(\#k) = (F, RA)$ |

In particular, both the maximum and the minimum values of the pairs (F, RA) are stored, thus identifying the plausible range of related physiological parameters. In particular, the minimum values set the Heart Rate limit towards the prediction algorithm is focused on. The matrix helps in rejecting values, possibly resulting from measurement affected by spurious noise, which are out of the plausible range and cannot represent any real physiological value. The adaptive control is based on such a matrix, which is continuously updated over the time. Hence, a new measurement is based on the previously stored parameters and so on.

The proposed method consists of two main phases:
1. Learning phase: this operating phase is meant to train and learn about the plausible physiological range of the subject. The learning phase operates both when the subject is sleeping and when the subject is certainly awake. Multiple factors are extracted through PPG technology as well as body context values (e.g. 3 axes wrist accelerations and gyroscope) to identify the patient awake signature. The pair values (F, RA) of the matrix are computed and stored. Additionally, the body context data are processed to identify the patient posture (walking, non-walking) and they are correlated with time-based PPG analysis output to identify the physiological conditions that defines when the patient is certainly awake. Worthy to note that the detection and prediction algorithm run in real time but the warning action, about the transition from D to S phases is disabled. However, the system is able to detect the irregularity of some physiological parameters (e.g. HRV, sudden decrease of HR, sudden drop in BP, . . . ). Consequently, the system can automatically inform a remote call centre about a potential risky situation for the health of the subject.

The learning phase is performed:
  a. As initial set-up, for the duration of about 8 hours the first time the wearable CPS is provided to the subject. The duration of the set-up phase ($T_{set-up}$) is a calibratable.
  b. On-demand, after the initial-set up, each time the subject activates the learning phase by activating it on the wearable CPS. In this case, the on-demand learning phase lasts for 10 minutes. The duration of the "on-demand" phase ($T_{on-demand}$) is calibratable.

2. Prediction phase, during which the body context data and PPG data are acquired to identify impending drowsy condition. The accelerometer and gyroscope data are processed to identify when the subject is resting (e.g., not walking/running), while PPG data are processed according both to the frequency-based and the time-based analyses. Based on the output of the processing and on the learning phase, the method produces a warning indicator when the subject is entering into drowsy state.

Figure 23:
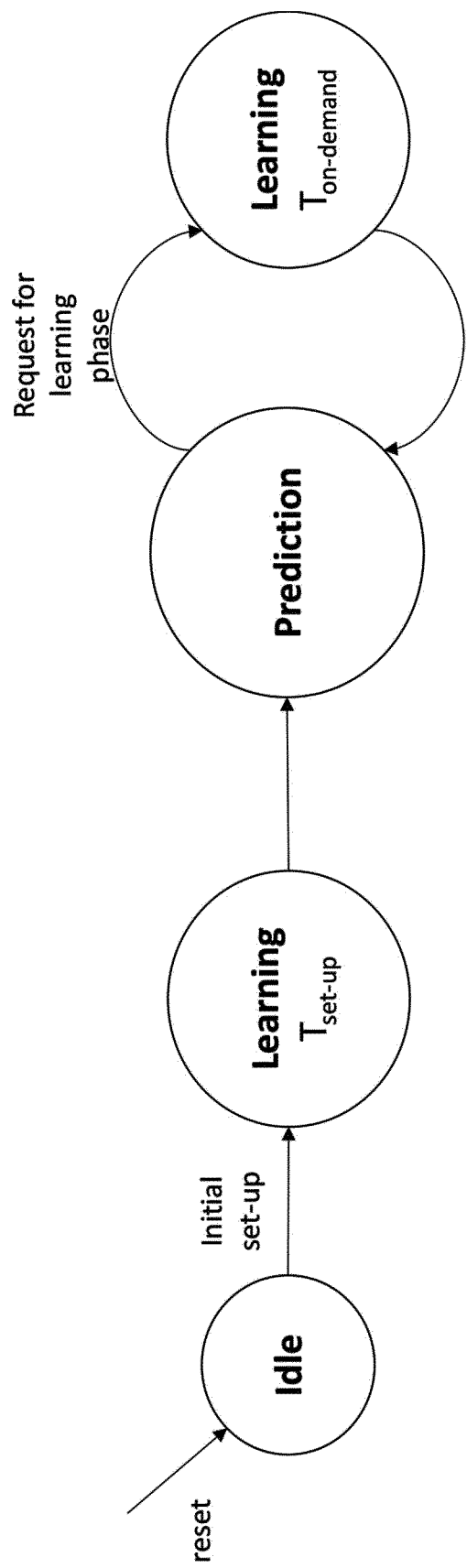
FIG. 23 shows a state diagram of Learning and Prediction phases of the present invention.

The above-described operating phases are regulated according to the state diagram shown in FIG. 23.

The range of meaningful factors supporting the implementation of the methodology for the detection and prediction of the W-D-S phases has been previously described. The list of physiological parameters is not exhaustive and can be enriched over the time. The methodology is flexible and will be able to integrate further details given a sufficient processing capability on the CPS.

Figure 24:
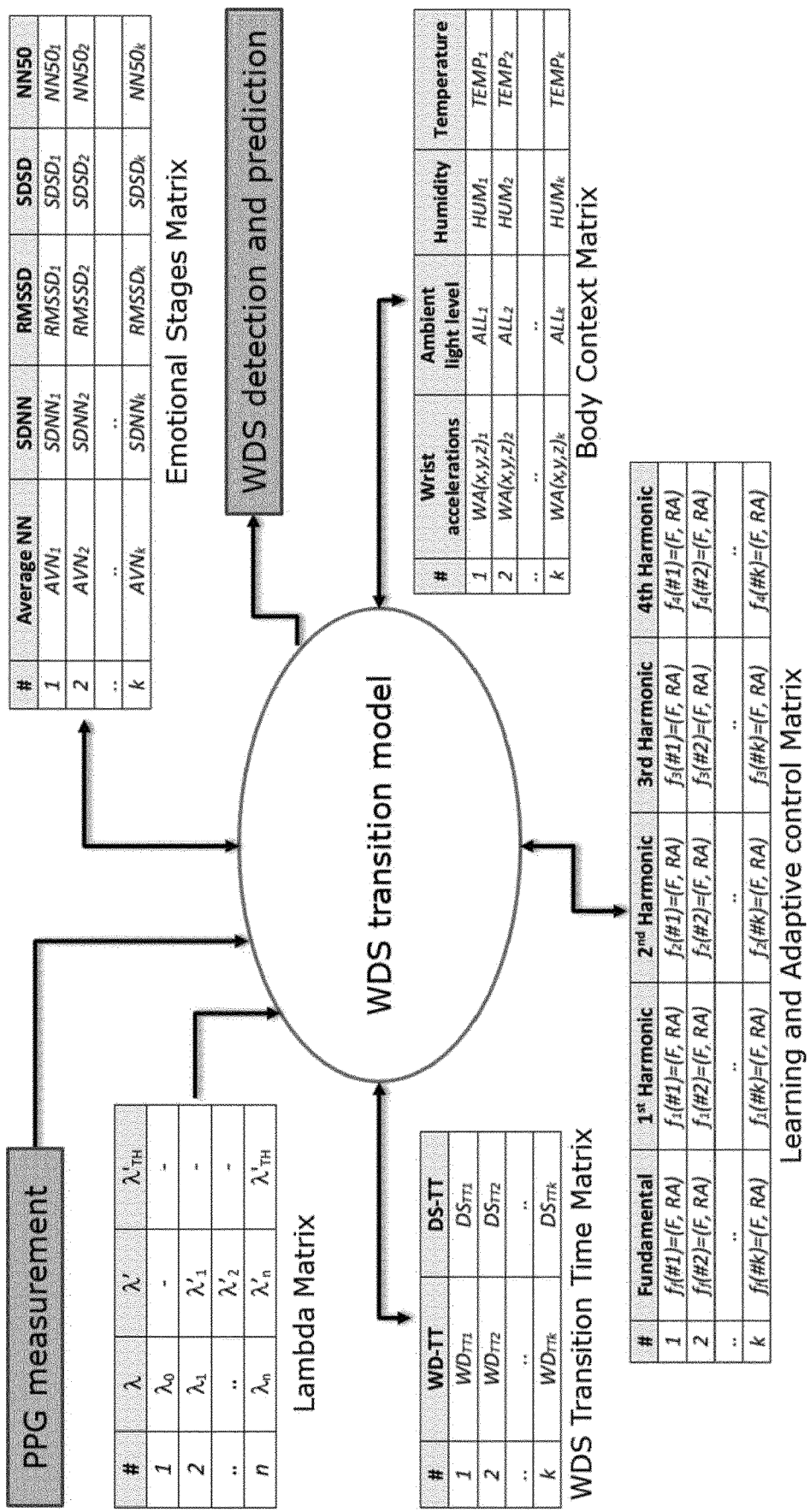
FIG. 24 shows WDS transition model and dependencies

The prerequisite of the methodology is the availability of an exhaustive (e.g., gender, age and weight of healthy subjects) and statistically significant proprietary database filled in with high quality raw physiological parameters. Thanks to the database, it is possible to develop a "WDS transition model" shown in FIG. 24 and to train either a neural network or a similar cognitive structure, defining also a set of default values useful to start the learning phase.

The WDS transition model describes the behavioural states and connects the W to S phases through the D phase. The WDS model is fed by multiple factors extracted from the PPG signal (e.g., fundamental frequency, harmonics and related amplitudes, $\lambda$, $\lambda'$, $\lambda'_{TH}$) including inputs related to the emotional states as well as subject's body context.

The starting point of the implementation refers to the learning process. The CPS will create, at first, the Learning and Adaptive control Matrix (LAM) by automatically measuring the frequencies (F) and relative amplitudes (RA) pair of values. This operation will be run the very first time of operation, by identifying the frequency extremes of the pairs over a large measurement period, possibly including sleep phases (e.g., overnight). This process is fully transparent to the subject, who is only responsible to activate the learning mode.

Then, the process can be repeated, later on and during the next days after the first initialisation, and the LAM will be updated with more refined values, better describing the extreme frequency values. Those values identify precisely the status of the subject in two very distinct phases, awake and sleep, since they are tightly connected to HR.

By looking back at the time history, from S to W phases, it is possible to identify the D phase through the above-described analysis of the trend of the PPG signal. Most importantly, it is also possible to measure the average time between W, D and S phases.

Those values feed a WDS-TT (Transition Time) Matrix as shown below, which is continuously updated, during operation, thus improving the confidence level of such a measurement.

| # | WD-TT | DS-TT |
|---|---|---|
| 1 | $WD_{TT1}$ | $DS_{TT1}$ |
| 2 | $WD_{TT2}$ | $DS_{TT2}$ |
| ... | ... | ... |
| k | $WD_{TTk}$ | $DS_{TTk}$ |

Through those values, it is also possible to define the starting positions of the sliding windows both in the frequency (SW-F) and relative amplitude (SW-RA) domains.

Once the subject enables the "prediction" mode, the windows start tracking the movement of frequencies and relative amplitudes, during the operation, based on the LAM and WDS-TT matrixes. This mechanism is able to follow the evolution of the PPG signal from W to S phases. The system recognizes when the subject is moving towards the D phase through the relative movement of the sliding windows, as shown in FIG. 15. Based on the WDS matrix, the CPS can predict the time when the subject could potentially enter into the S phase.

The basic functionality of the method describes the status of the subject in an almost ideal situation, without taking into account other factors.

Then, the real time concurrent analysis of several additional parameters will support the even more accurate and reliable prediction process.

In fact, the analysis of the emotional phases, as previously described, can significantly influence the prediction process.

Given the same fatigue conditions of the subject, a stress condition can alter the level of attention of the subject thus prolonging the time transition towards the D phase. For this reason, an Emotional Phases Matrix (ESM) as shown below, including the Average NN, SDNN, RMSSD, SDSD and NN50, is created and continuously updated.

The same holds for the dimensional state vector v(t), the chaotic attractor, and the Largest Lyapunov Exponent. If those values exceed a defined set of thresholds, the drowsiness prediction horizon is moved forward.

| # | Average NN | SDNN | RMSSD | SDSD | NN50 |
|---|---|---|---|---|---|
| 1 | $AVN_1$ | $SDNN_1$ | $RMSSD_1$ | $SDSD_1$ | $NN50_1$ |
| 2 | $AVN_2$ | $SDNN_2$ | $RMSSD_2$ | $SDSD_2$ | $NN50_2$ |
| ... | ... | ... | ... | ... | ... |
| k | $AVN_k$ | $SDNN_k$ | $RMSSD_k$ | $SDSD_k$ | $NN50_k$ |

The context details, relative to actual body position and generic health status of the subject, such as for example 3 axes wrist accelerations, ambient light level, humidity and temperature measured on the wrist are stored in a Body Context Matrix (BCM) shown below.

| # | Wrist accelerations | Ambient light level | Humidity | Temperature |
|---|---|---|---|---|
| 1 | $WA(x, y, z)_1$ | $ALL_1$ | $HUM_1$ | $TEMP_1$ |
| 2 | $WA(x, y, z)_2$ | $ALL_2$ | $HUM_2$ | $TEMP_2$ |
| ... | ... | ... | ... | ... |
| k | $WA(x, y, z)_k$ | $ALL_k$ | $HUM_k$ | $TEMP_k$ |

The information related to humidity is useful also for the emotional phases analysis. The other information available in the BCM can be used for:

a) the artefacts removal due to pronounced movement of the wrist, which could significantly affect the PPG measurement;

b) calibration of PPG when the subject has a flu or similar (e.g. temperature);

c) the validation of the sleep status (e.g. if the wrist of the subject is moving for a defined amount of time, to be calibrated, it is most likely not sleeping and vice versa).

The learning phase is used to identify the physiological signature of the subject when awake, as defined by the value $\lambda'_{TH}$ which is computed as follows.

The identification of signal peaks, in the time domain, is necessary to derive the status of the subject. It is performed by identifying the maximum (peak) of the function in each second. Once the maximum of the function has been identified in each time slot (for instance 1 second, to be calibrated), the outliers can be computed as the number of peaks that deviate from the average value (computed in 10 minutes) for a quantity greater than 10%:

$$\text{Outliers} = \frac{\text{\# peaks} \notin [(1-0.1) \cdot \overline{\text{peaks}}, (1+0.1) \cdot \overline{\text{peaks}}]}{\text{length (peaks)}}$$

When the time-based PPG analysis indicated the subject is certainly awake, the following tasks are performed:

The PPG signal is sampled for a duration of 60 seconds, with a sampling frequency of 20 Hz, obtaining the PPG(t) signal;

The FFT of PPG(t) is computed to provide the Power Spectrum Density PSD(f);

Two points are selected in the PSD(f):
  LF is the maximum of PSD(f), in the range 0.04 Hz<=f<0.15 Hz
  HF is the maximum of PSD(f), in the range 0.15 Hz<=f<=0.4 Hz The value $\lambda$=LF/HF is computed.

The above procedure is repeated for 10 minutes (to be calibrated), obtaining the set $\Lambda=\{\lambda_0, \lambda_1, \ldots, \lambda_9\}$; then, the differential set $\Lambda'=\{\lambda'_1, \lambda'_2, \ldots \lambda'_9\}$ is computed where $\lambda'_i = \lambda_{i-1} - \lambda_i$. The value $\lambda'_{TH}$ is computed as the average of the value $\Lambda'$ multiplied by an appropriate constant $\lambda_k$, which is tuned during the learning phase (personalized on the specific subject). During initial set-up the procedure is repeated during a time span of 8 hours (to be calibrated) each time the time-based PPG analysis as well as accelerometer/gyroscope data indicates the subject is awake. During on-demand learning, the process is repeated every time the phase is activated.

Hence, the prediction phase analyses the PPG signal to identify the drowsy condition as follows:
- The PPG signal is sampled for a duration of 60 seconds (to be calibrated), with a sampling frequency of 20 Hz (to be calibrated), obtaining the PPG(t) signal;
- The FFT of PPG(t) is computed to provide the Power Spectrum Density PSD(f);
- Two points are selected by analysing PSD(f):
  - LF is the maximum of PSD(f) in the range 0.04 Hz<=f<0.15 Hz
  - HF is the maximum of PSD(f) in the range 0.15 Hz<=h<=0.4 Hz
- The value $\lambda$=LF/HF is computed.

The above procedure is repeated for 10 minutes (to be calibrated, as above), obtaining the set $\Lambda = \{\lambda_0, \lambda_1, \ldots, \lambda_9\}$; then, the differential set $\Lambda' = \{\lambda'_1, \lambda'_2, \ldots \lambda'_9\}$ is computed where $\lambda'_i = \lambda_{i-1} - \lambda_i$.

After computing the two sets $\Lambda$ and $\Lambda'$, the number D of occurrences in $\Lambda'$ where $\lambda'_i > \lambda'_{TH}$ is computed.

The subject behaviour is defined as follows:
- If D==5, then subject is showing signals of an impending drowsy condition;
- If D>5, an alarm is produced as the subject is into drowsy condition.

As previously mentioned, the assessment of the emotional phases of the subject could affect the prediction's time horizon.

Hence a constant $ES_k$, which is calibrated run-time on the specific subject and stems from previous analysis supported by the proprietary data base, could be applied on top of the D value, thus resulting in:

$$D_{ES} = D + ES_k$$

Basically, it postpones the time horizon which is indicated by the forecast method as the likely drowsy occurrence.

Figure 25:
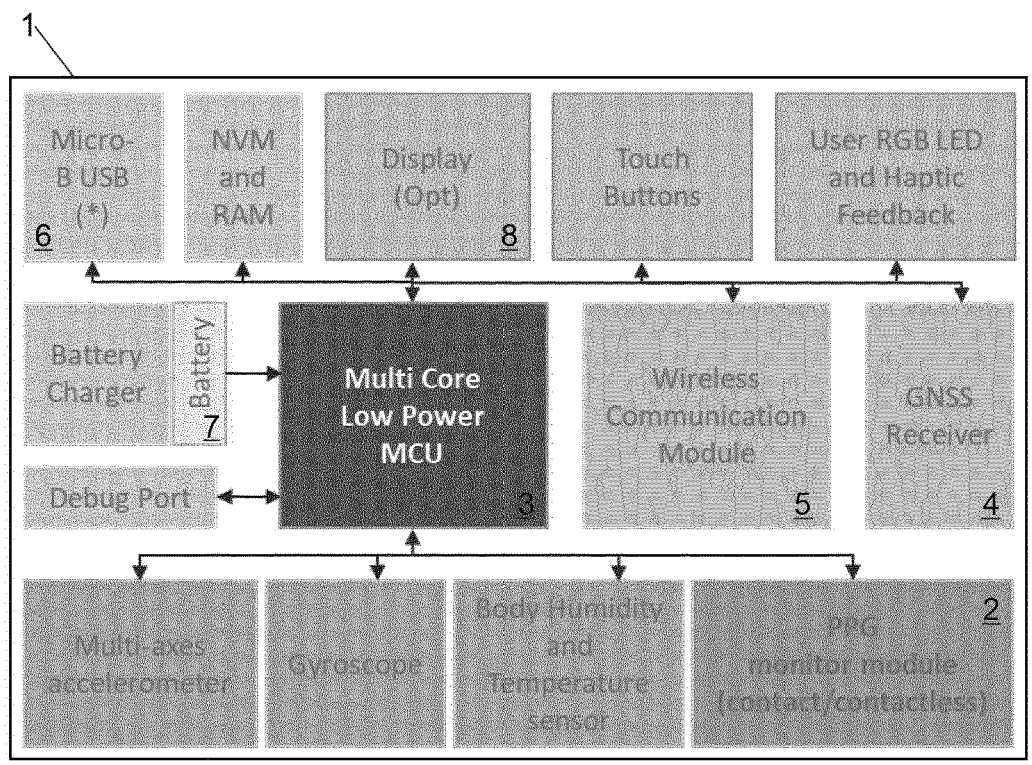
FIG. 25 shows a block diagram of a Cyber Physical System (CPS) according to the present invention.

The present invention is implemented by the CPS, a block diagram of which is shown in FIG. 25, where the CPS is referenced as a whole with reference numeral 1.

As may be appreciated, the CPS is based on a modular and composable HW architecture and on state-of-the-art semiconductor technology in order to cover a wide range of possible applications, whenever the level of attention of the subject is relevant (e.g. driving a vehicle, controlling a robot, working in a production manufacturing plant, etc.).

The modular and composable HW architecture covers both contact (e.g., a wearable CPS) and contactless (e.g., RADAR technology) applications. In fact, the PPG monitor module, referenced with reference numeral 2, may be either a classical contact sensor or a contactless PPG sensor. In both cases, the proposed CPS is able to extract the relevant features from the PPG signal outputted by the PPG monitor module and perform the previously described real-time analysis on an embedded low power microcontroller (MCU), referenced with reference numeral 3.

Particular attention has been devoted to the "connectivity" of the CPS in order to take into account the technological evolution over the years, wherein:

- GNSS (Global Navigation Satellite System) receiver, referenced with reference numeral 4, is meant to support any satellite navigation system technology providing autonomous geo-spatial positioning with global coverage. It includes e.g. the GPS, GLONASS, Galileo, Beidou and other regional systems;
- Wireless Communication Module, referenced with reference numeral 5, is meant to comprise any modem able to exchange data over either a wireless short range communication link (e.g. BLE, WiFi, ZigBee, etc.) or a wireless long range communication link (e.g. 2.5G, 3G, 4G, LTE, 5G, LPWAN, NB-IoT, LoRa . . . etc.); and
- Micro B-USB, referenced with reference numeral 6, is used as a common standard to interconnect nomadic devices towards PC and power supply, but any other suitable interfaces can be integrated over the years, according to the technological evolution.

The CPS 1 is self-powered, through a rechargeable battery, referenced with reference numeral 7, and uses low-power technologies in order to guarantee an excellent duration.

The display, referenced with reference numeral 8, is optional since there are potential low-cost applications, such as the "smart wearable tag" described below, which operates without a display.

The CPS 1 is able to transmit the measured data over a wireless communication link by means of a dedicated modem and the associated antenna subsystem. Depending on the specific implementation requirements, the CPS 1 may adopt either a short-range radio communication such as, for example, Bluetooth Low Energy (BLE), Wi-Fi, ZigBee, etc., or a long-range radio communication including, for example, 2.5G, 3G, 4G, LTE, 5G, NB-IoT, LoRa, etc.

When short range communication is used, measured data are transmitted by the CPS 1 to a gateway device, such as, for example, a personal mobile device, a smartphone, a tablet, an access-point, etc. The gateway device then relays the received data to a dedicated remote storage and processing IT platform.

When long-range communication is used, measured data are directly transmitted by the CPS 1 to a dedicated remote storage and processing IT platform.

Location can also be measured by the CPS 1 thanks to a GNSS receiver 4 able to support any satellite location technology.

Figure 26:
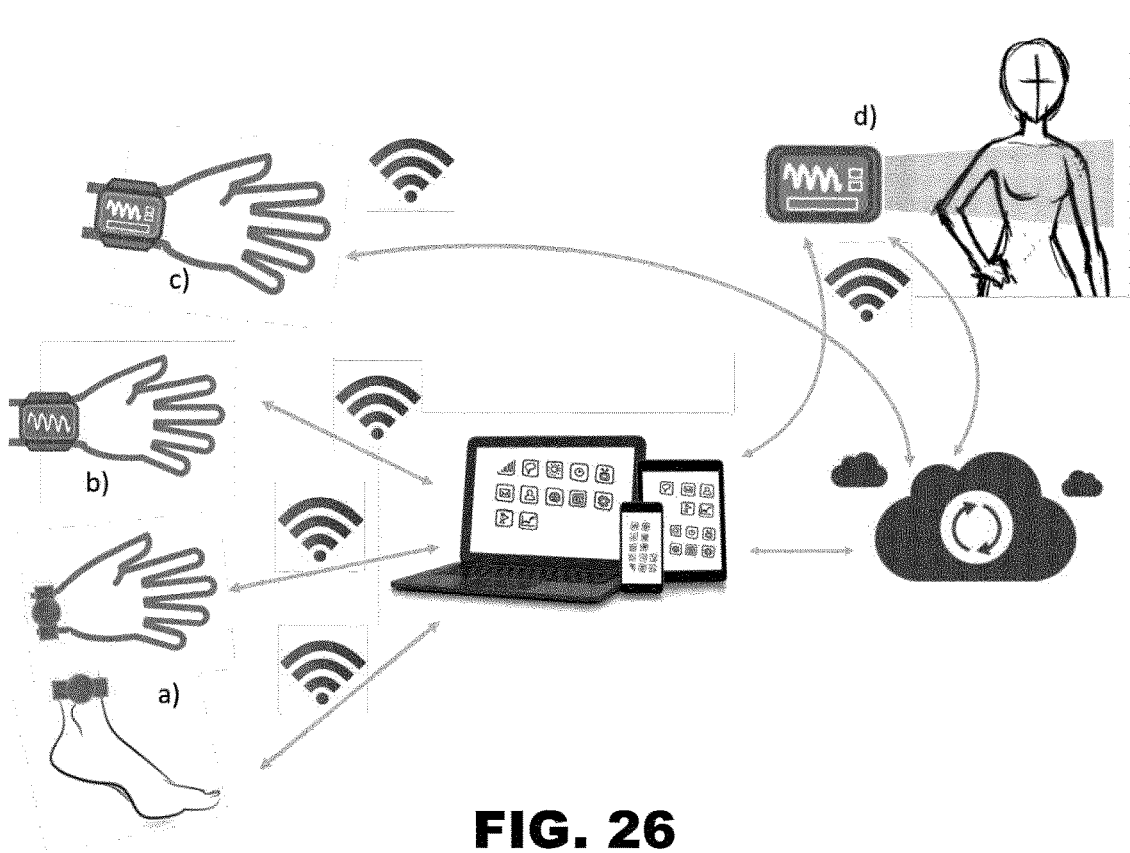
FIG. 26 shows the System Modularity in the form of a smart wearable tag (a), a smart wearable gateway (b), a smart contact drowsiness watcher (c), and a smart contactless drowsiness watcher.

The modularity of the CPS 1 is shown in FIG. 26.

First, a "smart wearable tag" (a) can be integrated in a medical bend and can be successfully used in remote/home health monitoring of subjects. The smart wearable tag communicates with the user through nomadic devices since doesn't have any user interface. The measured data can be then transferred to a remote data centre while an alarm can be managed in real-time. The smart wearable tag interacts with the nomadic devices and then communicates to the cloud. There are some potential advantages in such a configuration:
- a) cost effective solution due to the lack of user interface
- b) re-usable
- c) simpler solution with respect to standard wearable solution which are difficult to be cleaned.

Then the CPS integrates the user interfaces (e.g. display and touch buttons) and can be more easily used as a standalone device. The CPS interacts with the nomadic devices and then communicates to the cloud and it is available into two different versions, in order to address different user requirements and target costs.

The first version (b) transmits the measured data over a short-range communication to any device thus acting as a "smart wearable gateway".

Instead, the "smart contact drowsiness watcher" (c) supports long-range communication and then measured data are directly transmitted by the CPS to a dedicated remote storage and processing IT platform.

Finally, the "smart contactless drowsiness watcher" (d) provides similar features, available on (c) but relying on contactless PPG technology. It is worthy to mention that, in this specific case, the CPS is not meant to be a wearable system but can be positioned close to the subject (e.g. close to the bed, wheelchair), thus acquiring the PPG details from the contactless PPG sensor. The potential application case is related to public health systems, hospitals where it will be possible to detect the status of the subject, with particular respect to elderly, in a fully non-invasive manner and reliable manner and automatically inform the professionals about any irregular conditions.

The proposed smart wearable system is innovative in the following aspects:
  a) Use of the sole PPG technology, to extract a limited set of rich physiological features from such a measurement, both in the contact and contactless operation mode, to identify the W-D-S behavioural phases and the transition between them.
  b) Use of the PPG technology to identify the changes in cardiocirculatory activity typical of the phase preceding the entry into the sleep phase (i.e. the drowsiness phase).
  c) Characterization of the awake (W), drowsiness (D), and sleep (S) phases based on the variation of the trend in the PPG waveform: irregular in the awake phase, regular in the sleep phase and towards a regular trend in the falling asleep phase.
  d) In the drowsiness phase, the PPG waveform progressively tends towards a regular trend if compared to the awake phase: this fundamental conclusion is the result of accurate and exhaustive clinical observations carried out by experts in the field of sleep medicine.
  e) Identification of signal signatures and signature windows of the PPG waveform for the detection of the W-D-S transition.
  f) Less-invasive and simplified approach for the precise detection of the W-D-S phases through the analysis of cardiorespiratory signals using either a wearable (i.e. contact) device or contactless smart device using the PPG technology and communicating wireless towards other systems.
  g) Use of the CPS where the detection and prediction algorithms, based on PPG technology, run; the results, aimed at monitoring the health status of the subject and/or predicting drowsiness (D) phase, are sent wireless either to the selected nomadic devices (e.g. smartphone, tablet computer), in the case of option (a) and (b), or directly to the cloud, in the case of option (c). Then it is possible to activate further actions, such as:
    1) interaction with an operator of the emergency call centre;
    2) interaction with selected nomadic devices in order to start activities aimed at regaining the attention of the subject;
    3) interaction with the Infotainment System of the vehicle;
    4) providing several haptic feedbacks (e.g. acoustic, vibration);
  h) features extraction both in the frequency and in the time domain with the aim of capturing representative patterns and signature of PPG trends;
  i) self-calibration procedure and error validation techniques applied to the PPG signal in order to address a wide range of application in different domains;
  j) the methodology will be able to provide several feedback (e.g. acoustic, vibration, automatic call to an emergency centre) to the subject in order to gain his/her full attention from an incoming drowsiness state;
  k) introduces a multi-factors analysis based on the combination of different physiological parameters, extracted from PPG waveform, with emotional phases and context details of the subject;
  l) introduces a multi-domain approach based on the combination of time domain and frequency domain analysis of the acquired physiological parameters;
  m) the multi-factors and multi-domain approach provides meaningful information even in the case of low quality and noisy measurements of physiological parameters, which is normally the case;
  n) the multi-factors and multi-domain approach can be successfully automatized due to its inherent robustness;
  o) includes a learning and adaptive control, which is fully automated, transparent to the user and evolves, over the time, for the individual self-calibration of physiological parameters of the subject;
  p) runs in real-time and continuously adjusts the control parameters in order to provide the most accurate prediction capability;
  q) operates both with contact PPG and contactless PPG technology;
  r) possible exploitation in different application domains, where the identification of the W-D-S phases, and particularly the D one, are relevant;
  s) definition of a flexible and modular architecture of the Cyber Physical System in order to accommodate different algorithms (e.g. detection, prediction) over the life time.

The invention claimed is:
1. An electronic processing system designed to real-time detect one or more of awake (W), Drowsiness (D), and Sleep(S) phases of a subject, and/or predict transitions between at least awake (W) phase and either Drowsiness (D) or Sleep(S) phase of the subject based on photoplethysmography (PPG) technology and related physiological parameters of the subject measured via either a contact or a contactless photoplethysmography (PPG) sensor;
  the electronic processing system is programmed to:
   acquire a raw PPG signal from either the contact or the contactless PPG sensor, wherein the raw PPG signal reflects microvascular blood volume changes in a tissue bed beneath skin of the subject; analyze the raw PPG signal in both time and frequency domains by performing the following steps:
    detecting one or more of awake (W), Drowsiness (D), and Sleep(S) phases of a subject based on an output of the analysis of the raw PPG signal, and
    predicting transitions between at least awake (W) phase and either Drowsiness (D) or Sleep(S) phase of the subject based on the output of the analysis of the raw PPG signal;
    predicting an impending drowsy condition based on the output of the analysis of the raw PPG signal; and
    generating a warning signal when an impending drowsy condition is predicted;

outputting an alert to the subject in response to the warning signal to awaken the subject from the impending drowsy condition;

wherein the electronic processing system is further programmed to analyse the raw PPG signal in the frequency domain by:

computing a Power Spectrum Density (PSD) of the raw PPG signal, computing a maximum amplitude of the PSD in a low frequency range thereof and a maximum amplitude of the PSD in a high frequency range thereof, computing a ratio ($\lambda$) between the computed maximum amplitudes;

searching for consecutive peaks in the raw PPG signal;

computing one or more quantities based on consecutive peaks found; and predicting transitions between at least awake (W) phase and either Drowsiness (D) or Sleep(S) phases of the subject based on the computed quantities;

and wherein the electronic processing system is further programmed to predict onset of sleep in the subject based on a behaviour of the computed ratio ($\lambda$) over time, and wherein the computed quantities comprise:

an absolute value of a difference between a maximum and a given percentile of peak amplitude; and a percentage of peaks out of a given range centered on a mean of peaks.

2. The electronic processing system of claim 1, further programmed to compute additional quantities based on the raw PPG signal and indicative of emotional phases and stress levels of the subject;

the additional quantities comprise one or more of:

an average time between normal heartbeats (NN), a standard deviation of the time between heartbeats (SDNN), a root mean square of successive differences of heartbeats (RMSSD), a standard deviation of successive differences (SDSD), a number of adjacent normal heartbeat intervals that differ from each other by more than a certain time period (NN50), and a chaotic attractor, and Largest Lyapunov Exponent (MLE).

3. The electronic processing system of claim 1, further programmed to:

compute additional body-context quantities based on data obtained from an accelerometer or gyroscope coupled to the electronic processing system;

process the body-context quantities to identify a posture of the subject; and correlate the body-context quantities with an output of the time-based analysis of the raw PPG signal to identify physiological conditions of the subject that define when the subject is awake.

4. The electronic processing system of claim 1, further programmed to predict onset of sleep in the subject based on a Transition Model describing transitions between awake (W) and sleep(S) phases through a drowsiness (D) phase based on multiple quantities extracted from the raw PPG signal via the frequency-based analysis;

wherein the Transition Model comprises a Learning and Adaptive control Matrix (LAM), containing pairs of frequencies (F) and relative amplitudes (RA) of a fundamental frequency and of one or more harmonics thereof in the frequency spectrum of the raw PPG signal;

the pairs of frequencies (F) and relative amplitudes (RA) in the Learning and Adaptive control Matrix (LAM) are indicative of a plausible physiological range of the subject both during awake (W) and sleep(S) phases.

5. The electronic processing system of claim 4, further programmed to construct the Transition Model via a learning technique comprising:

a Learning phase meant to train and learn about the plausible physiological range of the subject during awake (W) and sleep(S) phases, and during which an awake physiological signature of the subject and pairs of frequencies (F) and relative amplitudes (RA) in the Learning and Adaptive control Matrix (LAM) are computed and stored; and a Prediction phase, during which an impending drowsy condition is predicted based on the Transition Model and on an output of data from an accelerometer or gyroscope that is coupled to the electronic processing system indicative of when the subject is inactive.

6. The electronic processing system of claim 5, further programmed to perform the learning phase:

as an initial set-up of the electronic processing system, for a certain duration; and on-demand, after the initial-set up.

7. A modular composable electronic system comprising:

either a contact or a contactless photoplethysmography (PPG) sensor of claim 1 to output a raw photoplethysmography (PPG) signal; and the electronic processing system of claim 1 and in communication with the PPG sensor to receive the raw PPG signal therefrom.

8. A non-transitory computer-readable storage medium containing computer instructions that, when executed by the electronic processing system cause the electronic processing system to become programmed and to execute the computer instructions as claimed in claim 1.

9. The electronic processing system of claim 1, wherein the warning signal is transmitted to a nomadic device that delivers the output to the subject.

10. The electronic processing system of claim 9, wherein the nomadic device is a wearable device worn by the subject.

11. The electronic processing system of claim 10, wherein the wearable device includes a smart wearable tag.

12. The electronic processing system of claim 1, wherein the raw PPG signal, and data derived from the raw PPG signal are delivered to a remote data center for storage and coordination.

13. An electronic processing system designed to real-time detect one or more of awake (W), Drowsiness (D), and Sleep(S) phases of a subject, and/or predict transitions between at least awake (W) phase and either Drowsiness (D) or Sleep(S) phase of the subject based on photoplethysmography (PPG) technology and related physiological parameters of the subject measured via either a contact or a contactless photoplethysmography (PPG) sensor;

the electronic processing system is programmed to:

acquire a raw PPG signal from the contact or the contactless PPG sensor, wherein the raw PPG signal reflects microvascular blood volume changes in a tissue bed beneath skin of the subject;

analyze the raw PPG signal in both time and frequency domains by performing the following steps:

detecting one or more of awake (W), Drowsiness (D), and Sleep(S) phases of a subject based on an output of the analysis of the raw PPG signal, and predicting transitions between at least awake (W) phase and either Drowsiness (D) or Sleep(S) phase of the subject based on the output of the analysis of the raw PPG signal;

generating a warning signal when a transition from the awake (W) phase toward either drowiness (D) or sleep(S) is predicted;

outputting an alert to the subject in response to the warning signal to awaken or reverse the transition of the subject toward drowsiness or sleep;

wherein the electronic processing system is further programmed to analyse the raw PPG signal in the frequency domain by:

computing a Power Spectrum Density (PSD) of the raw PPG signal, computing a maximum amplitude of the PSD in a low frequency range thereof and a maximum amplitude of the PSD in a high frequency range thereof, and computing a ratio ($\lambda$) between the computed maximum amplitudes; and searching for consecutive peaks in the raw PPG signal;

computing one or more quantities based on consecutive peaks found; and predicting transitions between at least awake (W) phase and either Drowsiness (D) or Sleep(S) phases of the subject based on the computed quantities;

wherein the electronic processing system is further programmed to predict onset of sleep in the subject based on a behaviour of the computed ratio ($\lambda$) over time, and wherein the computed quantities comprise:

an absolute value of a difference between a maximum and a given percentile of peak amplitude; and a percentage of peaks out of a given range centered on a mean of peaks.

14. An electronic processing system designed to real-time detect one or more of awake (W), Drowsiness (D), and Sleep(S) phases of a subject, and/or predict transitions between at least awake (W) phase and either Drowsiness (D) or Sleep(S) phase of the subject based on photoplethysmography (PPG) technology and related physiological parameters of the subject measured via a contact or a contactless photoplethysmography (PPG) sensor;

the electronic processing system (3) is programmed to:

acquire a raw PPG signal from the contact or the contactless PPG sensor, wherein the raw PPG signal reflects microvascular blood volume changes in a tissue bed beneath the skin of the subject;

analyze the raw PPG signal in both time and frequency domains by performing the following:

detecting one or more of awake (W), Drowsiness (D), and Sleep(S) phases of a subject based on an output of the analysis of the raw PPG signal, and predicting transitions between at least awake (W) phase and either Drowsiness (D) or Sleep(S) phase of the subject based on the output of the analysis of the raw PPG signal;

predict onset of sleep in the subject based on a Transition Model describing transitions between awake (W) and sleep(S) phases through a drowsiness (D) phase based on multiple quantities extracted from the raw PPG signal via the frequency-based analysis, wherein the Transition Model comprises a Learning and Adaptive control Matrix (LAM) containing pairs of frequencies (F) and relative amplitudes (RA) of a fundamental frequency and of one or more harmonics thereof in the frequency spectrum of the raw PPG signal, and the pairs of frequencies (F) and relative amplitudes (RA) in the Learning and Adaptive control Matrix (LAM) are indicative of a plausible physiological range of the subject both during awake (W) and sleep(S) phases;

generating a warning signal when a transition from the awake (W) phase toward either drowiness (D) or sleep(S) is predicted;

outputting an alert to the subject in response to the warning signal to awaken or reverse the transition of the subject toward drowsiness or sleep;

wherein the electronic processing system is further programmed to analyse the raw PPG signal in the frequency domain by:

computing a Power Spectrum Density (PSD) of the raw PPG signal, computing a maximum amplitude of the PSD in a low frequency range thereof and a maximum amplitude of the PSD in a high frequency range thereof, and computing a ratio ($\lambda$) between the computed maximum amplitudes; and wherein the electronic processing system is further programmed to predict onset of sleep in the subject based on a behaviour of the computed ratio ($\lambda$) over time.

15. An electronic processing system designed to real-time detect one or more of awake (W), Drowsiness (D), and Sleep(S) phases of a subject, and/or predict transitions between at least awake (W) phase and either Drowsiness (D) or Sleep(S) phase of the subject based on photoplethysmography (PPG) technology and related physiological parameters of the subject measured via either a contact or a contactless photoplethysmography (PPG) sensor;

the electronic processing system is programmed to:

acquire a raw PPG signal from either the contact or the contactless PPG sensor, wherein the raw PPG signal reflects microvascular blood volume changes in a tissue bed beneath skin of the subject; analyze the raw PPG signal in both time and frequency domains by performing the following steps:

detecting one or more of awake (W), Drowsiness (D), and Sleep(S) phases of a subject based on an output of the analysis of the raw PPG signal, and predicting transitions between at least awake (W) phase and either Drowsiness (D) or Sleep(S) phase of the subject based on the output of the analysis of the raw PPG signal;

predicting an impending drowsy condition based on the output of the analysis of the raw PPG signal; and generating a warning signal when an impending drowsy condition is predicted;

outputting an alert to the subject in response to the warning signal to awaken the subject from the impending drowsy condition;

wherein the electronic processing system is further programmed to analyse the raw PPG signal in the frequency domain by:

computing a Power Spectrum Density (PSD) of the raw PPG signal, computing a maximum amplitude of the PSD in a low frequency range thereof and a maximum amplitude of the PSD in a high frequency range thereof, and computing a ratio ($\lambda$) between the computed maximum amplitudes;

and wherein the electronic processing system is further programmed to:

predict onset of sleep in the subject based on a behaviour of the computed ratio ($\lambda$) over time, compute a set of differential ratios ($\lambda'$), wherein a differential ratio ($\lambda'$) is computed based on a difference between two temporally successive ratios ($\lambda$);

compute a number of occurrences in the set of differential ratios ($\lambda'$) of differential ratios ($\lambda'$) that meet a predetermined relationship with a threshold ratio ($A\lambda'_{TH}$) representing an awake physiological signature of the subject; and predict onset of sleep in the subject based on the computed number of occurrences.

16. The electronic processing system of claim 15, further programmed to compute the awake physiological signature of the subject based on the differential ratios ($\lambda'$) in the set of differential ratios ($\lambda'$), in particular as an average value of the differential ratios ($\lambda'$) multiplied by an appropriate constant ($\lambda_k$) tuned during a learning phase and peculiar to the subject.

* * * * *